United States Patent
Bengtsson et al.

(10) Patent No.: US 11,562,816 B2
(45) Date of Patent: Jan. 24, 2023

(54) SYSTEMS AND METHODS FOR ANALYSIS OF INSULIN REGIMEN ADHERENCE DATA

(71) Applicant: Novo Nordisk A/S, Bagsvaerd (DK)

(72) Inventors: Henrik Bengtsson, Taastrup (DK); Tinna Bjoerk Aradottir, Copenhagen (DK); Pete Brockmeier, Copenhagen (DK)

(73) Assignee: Novo Nordisk A/S, Bagsvaerd (DK)

(*) Notice: Subject to any disclaimer, the term of this patent is extended or adjusted under 35 U.S.C. 154(b) by 130 days.

(21) Appl. No.: 16/309,481

(22) PCT Filed: Jun. 22, 2017

(86) PCT No.: PCT/EP2017/065387
§ 371 (c)(1),
(2) Date: Dec. 13, 2018

(87) PCT Pub. No.: WO2018/001856
PCT Pub. Date: Jan. 4, 2018

(65) Prior Publication Data
US 2019/0131010 A1 May 2, 2019

(30) Foreign Application Priority Data
Jun. 30, 2016 (EP) .................................... 16177090

(51) Int. Cl.
*G16H 20/17* (2018.01)
*G16H 50/20* (2018.01)
*G16H 10/60* (2018.01)

(52) U.S. Cl.
CPC ............. *G16H 20/17* (2018.01); *G16H 10/60* (2018.01); *G16H 50/20* (2018.01)

(58) Field of Classification Search
CPC ............................... G16H 20/10; G16H 50/30
See application file for complete search history.

(56) References Cited

U.S. PATENT DOCUMENTS 9,734,302 B2   8/2017 Nielsen et al.
2007/0061166 A1* 3/2007 Ramasubramanian ..................... G16H 20/10
                                                                 705/2

(Continued)

FOREIGN PATENT DOCUMENTS

EP    2138944 A2   12/2009
EP    2568402 A1    3/2013

(Continued)

OTHER PUBLICATIONS

Tufts, Chris, "Pragmatic Stats: Variance," Mining the Details blog, Feb. 14, 2015 (Year: 2015).*

(Continued)

*Primary Examiner* — John P Go
(74) *Attorney, Agent, or Firm* — Wesley Nicolas

(57) ABSTRACT

Systems and methods for evaluating insulin medicament dosage regimen adherence by a subject are provided. A description of metabolic events the subject engaged in is obtained. Each event comprises a timestamp and a classification that is one of insulin regimen adherent and insulin regimen nonadherent. Events are binned into consecutive time windows on the basis of time to obtain a plurality of subsets. Adherence values are computed. Each adherence value is for a subset and is computed by dividing the insulin regimen adherent events by the total number of events in the subset. Adherence values are combined into a composite value by a process that comprises downweighting a first adherence value, representing a first time window, with respect to a second adherence value, representing a second time window, when the first time window occurs in time before the second time window. The composite value is communicated as a single representation.

19 Claims, 14 Drawing Sheets

(56) References Cited

U.S. PATENT DOCUMENTS

| | | | |
|---|---|---|---|
| 2007/0179352 A1 | 8/2007 | Randlov et al. | |
| 2008/0162182 A1* | 7/2008 | Cazares | G16H 40/67 |
| | | | 705/2 |
| 2009/0069745 A1* | 3/2009 | Estes | A61M 5/14244 |
| | | | 604/67 |
| 2009/0253970 A1 | 10/2009 | Bashan et al. | |
| 2010/0145174 A1 | 6/2010 | Alferness et al. | |
| 2010/0198021 A1* | 8/2010 | Alferness | G16H 20/60 |
| | | | 600/300 |
| 2010/0305975 A1* | 12/2010 | Daya | G06F 19/3462 |
| | | | 705/3 |
| 2011/0184752 A1 | 7/2011 | Ray et al. | |
| 2012/0095774 A1 | 4/2012 | Reinke et al. | |
| 2013/0218588 A1 | 8/2013 | Kehr et al. | |
| 2013/0317840 A1* | 11/2013 | Creswell | G06Q 50/22 |
| | | | 705/2 |
| 2014/0019396 A1 | 1/2014 | Carlsgaard et al. | |
| 2014/0118138 A1* | 5/2014 | Cobelli | A61B 5/4866 |
| | | | 340/539.12 |
| 2014/0172455 A1 | 6/2014 | Deng et al. | |
| 2014/0310598 A1 | 10/2014 | Sprague et al. | |
| 2014/0337047 A1* | 11/2014 | Mears | G16H 50/20 |
| | | | 705/2 |
| 2015/0006462 A1* | 1/2015 | Sudharsan | G06F 19/328 |
| | | | 706/52 |
| 2015/0130830 A1 | 5/2015 | Nagasaki et al. | |
| 2015/0217052 A1 | 8/2015 | Keenan et al. | |
| 2015/0217053 A1 | 8/2015 | Booth et al. | |
| 2015/0273147 A1* | 10/2015 | Duke | G16H 50/30 |
| | | | 604/504 |
| 2015/0309675 A1 | 10/2015 | Blinov et al. | |

FOREIGN PATENT DOCUMENTS

| | | | |
|---|---|---|---|
| JP | 2011147784 A | 8/2011 | |
| JP | 2015514483 A | 5/2015 | |
| JP | 2015118516 A | 6/2015 | |
| WO | 2006072416 A2 | 7/2006 | |
| WO | WO-2007149533 A2 * | 12/2007 | A61M 5/1723 |
| WO | 2010149388 A2 | 12/2010 | |
| WO | 2011082212 A1 | 7/2011 | |
| WO | 2012152295 A1 | 11/2012 | |
| WO | 2012152628 A1 | 11/2012 | |
| WO | 2012153295 A2 | 11/2012 | |
| WO | 2012156323 A1 | 11/2012 | |
| WO | 2014037365 A1 | 3/2014 | |
| WO | WO-2015040166 A1 * | 3/2015 | G01N 27/4166 |
| WO | 2015068815 A1 | 5/2015 | |

OTHER PUBLICATIONS

Anderson et al., "Selfreported compliance with insulin injection therapy in subjects with type 1 and 2 diabetes," 18th Congress of the International Diabetes Federation, Diabetologia, 2003, vol. 46, Suppl 2, A 275.

Andreas Thomas et al., "The "glucose pentagon": assessing glycemic control of patients with diabetes mellitus by a model integrating different parameters from glucose profiles," Diabetes Technology and Therapeutics, 2009, vol. 11, No. 6, pp. 399-409.

Burdick et al., "Missed insulin meal boluses and elevated hemoglobin A1c levels in children receiving insulin pump therapy", Pediatrics, 2004, vol. 113, No. 3, Pt. 1, pp. e221-e224.

DOCT Research Group, "The effect of intensive treatment of diabetes on the development and progression of long-term complications in insulin-dependent diabetes mellitus," N Engl J Med, 1993, vol. 329, No. 14, pp. 977-986.

Randløv et al., "How Much Do Forgotten Insulin Injections Matter to Hemoglobin A1c in People with Diabetes? A Simulation Study," Journal of Diabetes Science and Technology, 2008, vol. 2, No. 2, pp. 229-235.

Marc Weber et. al, Visualizing Time-Series on Spirals, http://ieg.ifs.tuwien.ac.at/~aigner/teaching/ws06/infovis_ue/papers/spiralgraph_weber01visualizing.pdf, accessed Feb. 10, 2017.

Anderson RT et al Self-reported compliance with insulin injection therapy in subjects with type 1 and 2 diabetes. 18th Congress of the International Diabetes Federation. Diabetologia. 2003;46(Suppl 2):A 275; Abstract 795.

Burdick J, et al Missed insulin meal boluses and elevated hemoglobin A1c levels in children receiving insulin pump therapy. Pediatrics. Mar. 2004;113 Issue 3 :e221-4.

Randloev and Poulsen. How Much Do Forgotten Insulin Injections Matter to Hemoglobin A1c in People with Diabetes? A Simulation Study. Journal of Diabetes Science and Technology; Mar. 2008 vol. 2 No 2 pp. 229-235.

The Diabetes Control and Complications Trial Research Group. The effect of intensive treatment of diabetes on the development and progression of long-term complications in insulin-dependent diabetes mellitus. N Engl J Med. 1993 vol. 329 No. 14 pp. 977-986.

Thomas A, et al The "glucose pentagon": assessing glycemic control of patients with diabetes mellitus by a model integrating different parameters from glucose profiles. Diabetes Technology and Therapeutics; 2009 vol. 11 No. 6 pp. 399-409.

Weber et al "Visualizing Time-Series on Spirals" http://ieg.ifs.tuwien.ac.at/~aigner/teaching/ws06/infovis_ue/papers/spiralgraph_weber01visualizing.pdf Accessed Aug. 5, 2016, 6 Pages.

Shinada et al., "Visualization Method of Time Series Data Based on "Snail-View"", Multimedia, Distributed, Cooperative, and Mobile Symposium (DICOMO 2008), Symposium collection of papers, Information Processing Society of Japan, Jul. 2008, vol. 2008, No. 1, pp. 1825-1803.

* cited by examiner

402 — Methods for evaluating historical adherence to a prescribed insulin medicament dosage regimen 206 for a subject using a device 250 are provided. A first data set 220 is obtained. The first data set comprises a plurality of metabolic events in which the subject engaged. The plurality of metabolic events are within a first period of time 222. Each respective metabolic event 224 in the plurality of metabolic events comprises (i) a timestamp 226 of the respective metabolic event and (ii) a classification 228 that is one of insulin regimen adherent and insulin regimen nonadherent.

404 — Each metabolic event in the plurality of metabolic events is a fasting event and the prescribed insulin medicament dosage regimen is a basal insulin medicament dosage regimen.

406 — Each metabolic event in the plurality of metabolic events is a meal event, and the prescribed insulin medicament dosage regimen is a bolus insulin medicament dosage regimen.

408 — Each respective metabolic event in the plurality of metabolic events is binned on the basis of a plurality of nonoverlapping consecutive primary time windows within the evaluation period. Each respective nonoverlapping consecutive primary time window 235 in the plurality of nonoverlapping consecutive primary time windows is of a same first fixed duration. Each respective metabolic event in the plurality of metabolic events is placed into a single respective nonoverlapping primary consecutive time window in the plurality of nonoverlapping consecutive time windows when the timestamp for the respective metabolic event is within the respective nonoverlapping consecutive primary time window, thereby obtaining a plurality of primary subsets of the plurality of metabolic events. Each respective primary subset 233 of the plurality of primary metabolic events in the plurality of primary subsets is for a different respective nonoverlapping consecutive primary time window in the plurality of nonoverlapping consecutive primary time windows.

410 — The same first fixed duration is a day, a week, two weeks, or a month.

412 — Compute a plurality of primary adherence values 230. Each respective primary adherence value 232 in the plurality of primary adherence values represents a corresponding primary subset in the plurality of primary subsets. Each respective primary adherence value in the plurality of primary adherence values is computed by dividing a number of insulin regimen adherent metabolic events in the corresponding primary subset in the plurality of primary subsets by a total number of metabolic events in the corresponding primary subset in the plurality of primary subsets.

Fig. 4A

414

Combine the plurality of primary adherence values into a primary composite adherence value 237. The combining downweights a first primary adherence value in the plurality of primary adherence values, representing a first primary time window in the plurality of nonoverlapping consecutive primary time windows, with respect to a second primary adherence value, representing a second primary time window in the plurality of nonoverlapping consecutive primary time windows, in calculating the primary composite adherence value, on the basis that the first primary time window occurs in time before the second primary time window.

416

The combining calculates the primary composite adherence value as:
$$\sum_{i=1}^{Q} w_i a_i$$
where,
$$\{w_1, \ldots, w_Q\} = \left\{\frac{1}{Q}, \ldots, \frac{Q}{Q}\right\},$$
each $a_i$ is a primary adherence value in the plurality of primary adherence values and occurs in time before $a_{i+1}$, and
each $w_i$ is an independent weight for a corresponding $a_i$.

418

The combining calculates the primary composite adherence value as:
$$\sum_{i=1}^{Q} w_i a_i$$
where,
each $a_i$ is a primary adherence value in the plurality of primary adherence values and occurs in time before $a_{i+1}$,
each $w_i$ is an independent weight for a corresponding $a_i$,
each $w_i$ is (i) equal to a first value when $w_i$ represents a primary time window that is before a threshold time and (ii) equal to a second value when $w_i$ represents a primary time window that is after the threshold time, and
the first value is smaller than the second value.

420

The threshold time is two weeks prior to when the combining is performed, four weeks prior to when the combining is performed, or six weeks prior to when the combining is performed.

422

The first value is zero and the second value is 1.

Fig. 4B

Bin each respective metabolic event in the plurality of metabolic events on the basis of a plurality of nonoverlapping consecutive secondary time windows within the first period of time.

Each respective nonoverlapping consecutive secondary time window 244 in the plurality of nonoverlapping consecutive secondary time windows is of a same second fixed duration other than the first fixed duration.

Each respective metabolic event in the plurality of metabolic events is placed into a single nonoverlapping secondary consecutive time window in the plurality of nonoverlapping consecutive secondary time windows when the timestamp for the respective metabolic event is within the single nonoverlapping consecutive secondary time window, thereby obtaining a plurality of secondary subsets of the plurality of metabolic events.

Each respective secondary subset 249 of the plurality of metabolic events in the plurality of secondary subsets is for a different secondary time window in the plurality of nonoverlapping consecutive secondary time windows.

A plurality of secondary adherence values 247 is computed. Each respective secondary adherence value 242 in the plurality of secondary adherence values represents a corresponding secondary subset in the plurality of secondary subsets.

Each respective secondary adherence value in the plurality of secdondary adherence values is computed by dividing a number of insulin regimen adherent metabolic events in the corresponding secondary subset in the plurality of secondary subsets by a total number of metabolic events in the corresponding secondary subset in the plurality of secondary subsets.

The plurality of secondary adherence values are combined into a secondary composite adherence value 243. The combining downweights a first secondary adherence value in the plurality of secondary adherence values, representing a first secondary time window in the plurality of nonoverlapping consecutive secondary time windows, with respect to a second secondary adherence value, representing a second secondary time window in the plurality of nonoverlapping consecutive secondary time windows, in calculating the secondary composite adherence value, on the basis that the first secondary time window occurs in time before the second secondary time window.

The communicating also communicates the secondary composite adherence value as a secondary single representation 245.

Fig. 4D

Basal regimen: take basal dose twice per day, one in the morning and one at night time (app. 12 hours between). The characterization of a metabolic event, being a fasting event, is provided as follows:

*For every date (primary period being a day and relevant period defined by the regimen being a day):*

> *Were two basal injections detected?*
> > *If no*
> > > *Metabolic event marked out of basal adherence, B2*
> > *If yes*
> > > *Was the time between basal injections >10 and <14 hours?*
> > > > *If yes*
> > > > > *Mark metabolic event as in basal and timing adherence, B1, C1*
> > > > *If no*
> > > > > *Mark metabolic event as in basal adherence, but out of timing adherence, B1, C1.*

Fig. 6

SYSTEMS AND METHODS FOR ANALYSIS OF INSULIN REGIMEN ADHERENCE DATA

CROSS-REFERENCE TO RELATED APPLICATIONS

This application is a 35 U.S.C. § 371 National Stage application of International Application PCT/EP2017/065387 (published as WO 2018/001856), filed Jun. 22, 2017, which claims priority to European Patent Application 16177090.4, filed Jun. 30, 2016, the contents of all above-named applications are incorporated herein by reference.

TECHNICAL FIELD

The present disclosure relates generally to systems and methods for assisting patients and health care practitioners in monitoring adherence to prescribed insulin medicament dosage regimens by providing a single representation or a pair of representations that indicate the overall adherence to such regimens.

BACKGROUND

Type 2 diabetes mellitus is characterized by progressive disruption of normal physiologic insulin secretion. In healthy individuals, basal insulin secretion by pancreatic β cells occurs continuously to maintain steady glucose levels for extended periods between meals. Also in healthy individuals, there is prandial secretion in which insulin is rapidly released in an initial first-phase spike in response to a meal, followed by prolonged insulin secretion that returns to basal levels after 2-3 hours.

Insulin is a hormone that binds to insulin receptors to lower blood glucose by facilitating cellular uptake of glucose, amino acids, and fatty acids into skeletal muscle and fat and by inhibiting the output of glucose from the liver. In normal healthy individuals, physiologic basal and prandial insulin secretions maintain euglycemia, which affects fasting plasma glucose and postprandial plasma glucose concentrations. Basal and prandial insulin secretion is impaired in Type 2 diabetes and early post-meal response is absent. To address these adverse events, patients with Type 2 diabetes are provided with insulin treatment regimens. Patients with Type 1 diabetes are also provided with insulin treatment regimens.

Some diabetic patients only need a basal insulin treatment regimen to make up for deficiencies in pancreatic β cells insulin secretion. Other diabetic patients need both basal and bolus insulin treatment. Patients that require both basal and bolus insulin treatment take a periodic basal insulin medicament treatment, for instance once or twice a day, as well as one or more bolus insulin medicament treatments with meals.

The goal of insulin treatment regimens is to achieve steady glucose levels. One way to measure their success is to take continuous glucose level measurements or to measure HbA1c levels. The term "HbA1c" refers to glycated haemoglobin. It develops when haemoglobin, a protein within red blood cells that carries oxygen throughout the body, joins with glucose in the blood, thus becoming "glycated." By measuring glycated haemoglobin (HbA1c), health care practitioners are able to get an overall picture of average glucose levels over a period of weeks/months. For people with diabetes, the higher the HbA1c, the greater the risk of developing diabetes-related complications Insulin treatment regimen nonadherence is a barrier that prevents diabetic patients from reaching suitable HbA1c goals. Insulin treatment regimen adherence is typically defined as the degree to which a patient correctly follows medical advice (e.g., a standing insulin treatment regimen for a subject comprising at least a basal insulin medicament dosage regimen), but can also be, for example, consistency in diet and exercise. The reasons for nonadherence are many and different. One reason for nonadherence is poor health literacy and comprehension of treatment. Patients fail to understand glucose measurement results, lack positive feedback when adherent, or feel a lack of urgency. Another reason for nonadherence is the fear of side effects. For instance, the fear of hypoglycaemia if the patient strictly adheres to the standing insulin regimen. Yet another reason for nonadherence is the hassle and time-consuming aspect of conventional standing insulin regimens, which often entail home-logging data and frequent injections and glucose measurements. Still another reason for nonadherence is an inability to pinpoint the source of nonadherence that is the actual source of the adverse effect on stable glucose levels.

International Publication Number WO 2012/152295 A2 to Insulin Medical Ltd. optimizes insulin absorption by using one or more sensors and actuators configured to provide data relating to a user's meal status, meal timing, the timing of administered drug, drug dose, drug type, the logging of user activity, and the analysis thereof. For instance, WO 2012/152295 A2 discloses a device that may be placed over an injection site or an injection port to treat the tissue at the injection site, while collecting information on the injected drug at the time of injections with an option to provide feedback to the user, such as alerts on missed injections. WO 2012/152295 A2 further discloses using meal data and other subject data, such as the activity of the subject, to facilitate mapping the subject activity relative to injection events and optionally meal events to provide for fine control of the systemic metabolic process of glucose and insulin and therefore minimize occurrence of post prandial hyperglycemic and hypoglycemic events. However, WO 2012/152295 A2 fails to provide satisfactory ways to determine and quantify the effects of insulin regimen adherence, or lack thereof, on the health of a subject (e.g., glucose levels of the subject). Moreover, generally, WO 2012/152295 A2 fails to provide overall feedback on the subject's adherence to an insulin medicament regimen.

International Publication Number WO 2014/037365 A1 to Roche Diagnostics GMBH describes methods and apparatuses for analyzing blood glucose data and events and, in particular, to computer implemented methods for visualizing correlations between blood glucose data and events associated with the blood glucose data such as meals. However, WO 2014/037365 A1 fails to disclose any categorization of meals in terms of insulin regimen adherence. Further, WO 2014/037365 A1 fails to provide satisfactory ways in which to determine and quantify the effects of insulin regimen adherence, or lack thereof, on the health of a subject.

US Publication Number US 2015/0006462 A1 describes a system for managing a patient's medical adherence, wherein the system is adapted for performing a method comprising receiving data related to a patient, the data including information related to a prescribed medication regimen having one or more medications, patient behavior data, a respective literacy level associated with each of the one or more medications. The method further comprises calculating a compliance to dosage and a compliance to time for each of the one or more medications based on the received data. Compliance to dosage, can for example be calculated as if a patient was prescribed 10 units of a medication in a day and took only 8 units, the respective compliance to disease is obtained by dividing the amount of units actually consumed by the prescribed units. In this instance it would be 0.8. Compliance to time, can for example be calculated as follows. For ten dosages prescribed throughout the day, the Boolean values may be utilized to calculate an overall value for the day. For example, if 8 out of 10 actual consumption times for a particular medication complied with the prescribed dosage times, then the actual consumption time would be assigned a "1" for those 8 instances and a "0" would be assigned for the other two instances. Accordingly a compliance value of 0.8 may be calculated for the compliance to time for that particular medicine by dividing the overall Boolean value with the total instances. The method further comprises calculating a drug adherence count associated with each of the one or more medications by summing at least two of the compliance to dosage, compliance to time and the respective literacy level associated with each of the one or more medications. The literacy level is a metric to assess the familiarity of a patient with a prescribed regimen and its medications, and it may be impacted based on the occurrence of a condition based on lack of medical adherence by a patient, e.g., effects based on user behaviour, such as lowering of blood sugar level due to missing medication. The method further comprises determining a daily medication adherence value and a daily medication adherence baseline value, and a threshold based on the ratio between the two values. The threshold can be used to determine whether an intervention is required. However, US 2015/006462 A1 fails to disclose how to automatically obtain metabolic events that are related to the prescribed insulin medicament dosage regimen, and thereby fails to systematically monitor adherence for a subject engaged in such metabolic events as a part of the daily routines. In fact US 2015/0006462 A1 suggests a generic method for any medicament, where it is assumed that the prescribed dose events are independent of the users behavior, e.g., 10 units or 10 doses are taken during a day or at prescribed times. Such a method would fail to track adherence, where the number of bolus injection events may vary due to user behavior, e.g., the user have more meals than expected. In general, US 2015/006462 A1 does not solve the problem of how to systematically allow tracking of adherence based on well defined reference points in time, and is limited to track adherence within the boundaries specified by periods, where the beginning of the period and the end of the period is pre-defined in relation to the structure of a calendar, e.g., 10 units during a day.

A drawback of adherence algorithms based on calendar periods can be explained by considering an example for a basal insulin dosage regimen specifying 1 bolus injection per day, in combination with an adherence tracking algorithm based on a calendar day of 24 hours. The calendar day starts at midnight. On the first day of the example basal insulin is injected at 23:00 PM, on the second day basal insulin is omitted, but on the third day basal insulin is injected at 00:30 AM, and 23:00 PM. In that case an adherence algorithm based on a 24 hours calendar day would characterize day 1 as in-adherence but day 2 and 3 as nonadherent. Three injections were applied with some degree of regularity, but only 1 out of three days were categorized in adherence. Although US 2015/006462 suggests that adherence can be a function of a time delay, this functional relation is only possible, if at well defined reference time is established, as is the case in the described example where insulin is to be injected a 2 PM with an expectation of a meal to be consumed at 2:30. However, as mentioned previously user behaviour does not always follow expectations and there can be drawbacks associated with the use of expectations for reference times, and as also mentioned there can be drawbacks associated with only using calendar days to establish a measure of basal adherence.

The described method of US 2015/0006462 comprises, calculating a drug adherence count serving as a metric that accounts for a consumed medication and may be calculated as the sum of at least two of the compliance with respective prescribed time of the day when it is supposed to be taken, compliance with respective prescribed dosage of the medication, and a patent literacy about the medications in the regimen. The described method further comprises determining a daily medication adherence, based on the drug adherence count and a drug importance factor, and a daily regimen adherence value can be calculated as a sum of the daily medication adherence for each individual medication.

However, for some purposes it is desired to have a single value being a metric of compliance over a larger time range, instead of detailed information of compliance on the individual days of the treatment. US 2015/0006462 fails to show a solution for this purpose, as it is not an object of the described method.

Given the above background, what is needed in the art are systems and methods that provide satisfactory ways to provide insulin regimen adherence feedback to diabetic patients or health care practitioners.

The object of the present disclosure is to provide systems and methods that provide satisfactory ways to provide insulin regimen adherence feedback to diabetic patients or health care practitioners.

SUMMARY

In the disclosure of the present invention, embodiments and aspects will be described, which will address one or more of the above objects or which will address objects apparent from the below disclosure as well as from the description of exemplary embodiments.

The present disclosure addresses the above-identified need in the art by providing methods and apparatus for assisting patients and health care practitioners in managing insulin delivery to diabetic patients. Using the systems and method of the present disclosure, a diabetic patient or a health care practitioner is provided with a single representation (e.g., a single number) that represents the insulin regimen adherence of the diabetic patient. Using this single representation, the effect of noncompliant meals, fasting events, bolus injections, or basal injections on glucose levels on the health of the patient can be ascertained.

Thus, the present disclosure relates to the computation, processing, and visualization of prescribed insulin medicament dosage regimen adherence data that provides a patient and/or a health care practitioner with the ability to monitor insulin regimen adherence and thereby the ability to see how such regimen adherence adversely or beneficially affects patient health.

In one aspect of the present disclosure, systems and methods are provided for evaluating historical insulin regimen adherence to a prescribed insulin medicament dosage regimen for a subject. A first data set is obtained. The first data set comprises a plurality of metabolic events the subject engaged in over an evaluation period. Each respective metabolic event in the plurality of metabolic events comprises (i) a timestamp of the respective metabolic event and (ii) a classification that is at least one of "insulin regimen adherent" and "insulin regimen nonadherent."

Each respective metabolic event in the plurality of metabolic events is binned on the basis of a plurality of non-overlapping consecutive primary time windows within the evaluation period. Each respective nonoverlapping consecutive primary time window in the plurality of nonoverlapping consecutive primary time windows is of a same first fixed duration (e.g., a day, a week, two weeks, or a month). In this binning process, each respective metabolic event in the plurality of metabolic events is placed into a single respective nonoverlapping (consecutive) primary time window in the plurality of nonoverlapping consecutive time windows when the timestamp for the respective metabolic event is within the respective nonoverlapping consecutive primary time window. In this way, a plurality of primary subsets of the plurality of metabolic events is obtained, where each respective primary subset of the plurality of metabolic events in the plurality of primary subsets is for a different respective nonoverlapping consecutive primary time window in the plurality of nonoverlapping consecutive primary time windows.

Next, a plurality of primary adherence values is computed. Each respective primary adherence value in the plurality of primary adherence values represents a corresponding primary subset in the plurality of primary subsets. Each respective primary adherence value in the plurality of primary adherence values is computed by dividing a number of insulin regimen adherent metabolic events in the corresponding primary subset in by a total number of metabolic events in the corresponding primary subset.

The plurality of primary adherence values is combined into a primary composite adherence value. In so doing, a first primary adherence value, representing a first primary time window in the plurality of nonoverlapping consecutive primary time windows, is downweighted with respect to a second primary adherence value, representing a second primary time window in the plurality of nonoverlapping consecutive primary time windows, on the basis that the first primary time window occurs in time before the second primary time window.

The primary composite adherence value is then communicated (e.g., to a display, to a remote device, to a database, etc.) as a primary single representation. In this way, the historical insulin regimen adherence of the subject to the standing insulin medicament dosage regimen is evaluated.

Hereby is provided a system and method which establishes adherence monitoring based on metabolic events, which the subject actually engaged in, and thereby eliminates the risk of user behaviour not always follows expectations. The system and the method solves the problem of how to systematically allow tracking of periodic adherence or nonadherence based on well defined and reliable reference points in time. As the data set only comprises metabolic events that the subject engaged in, the system and the method does not rely on input on a user response, and it thereby solves the problem of prior art. As the data set comprises timestamps for each metabolic event, which the subject engaged in the adherence is monitored with a high degree of uncertainty. The use of data comprising metabolic events that the subject actually engaged in for the purpose of monitoring adherence has not been previously used or described, nor has the importance of using such data in order to minimize uncertainty of the monitored adherence.

In a further aspect, the timestamp of the metabolic event is derived from autonomously timestamped measurements of an indicator of the metabolic event.

In a further aspect, the timestamp of the metabolic event is derived from autonomous timestamped glucose measurements, wherein the glucose measurements is an indicator of the metabolic event, i.e., the glucose measurement is a measurement of the glucose concentration in the blood stream.

In a further aspect, the timestamp of the metabolic event is derived from autonomous timestamped glucagon, lipids or amino acids measurements, wherein the glucagon, lipids or amino acid measurements are indicators of the metabolic event, i.e., the measurements are measurements of the concentration of the respective molecules in the blood stream.

In a further aspect, autonomous measurements are measurements obtained by a measuring device, wherein the measuring is undertaken or carried on without outside control of a user. Hereby is provided data that do not rely on input controlled by the subject or an operator of the device.

In a further aspect, autonomous measurements are measurements obtained by a device measuring at a specified or a variable frequency In some embodiments, the plurality of primary adherence values are combined to calculate the primary composite adherence value using the equation:

$$\sum_{i=1}^{Q} w_i \alpha_i$$

where, $$\{w_1, \ldots, w_Q\} = \left\{\frac{1}{Q}, \ldots, \frac{Q}{Q}\right\},$$

each $a_i$ is a primary adherence value in the plurality of primary adherence values and occurs in time before $a_{i+1}$, and each $w_i$ is an independent weight for a corresponding $a_i$.

In alternative embodiments, the plurality of primary adherence values are combined to calculate the primary composite adherence value using the equation:

$$\sum_{i=1}^{Q} w_i \alpha_i$$

where, each $a_i$ is a primary adherence value in the plurality of primary adherence values and occurs in time before $a_{i+1}$, each $w_i$ is an independent weight for a corresponding $a_i$, each $w_i$ is (i) equal to a first value when $w_i$ represents a primary time window that is before a threshold time and (ii) equal to a second value when $w_i$ represents a primary time window that is after the threshold time, and the first value is smaller than the second value. In some such embodiments, the threshold time is two weeks prior to when the combining is performed, four weeks prior to when the combining is performed, or six weeks prior to when the combining is performed. In some embodiments, the first value is zero and the second value is 1.

In some embodiments, the plurality of primary adherence values are combined to calculate the primary composite adherence value using the equation:

$$\sum_{i=1}^{Q} w_i a_i$$

where each $a_i$ is a respective primary adherence value in the plurality of primary adherence values, each $a_i$ occurs in time before and $w_i$ is a weighting factor that is computed as a linear function of time such that $w_i$ is less than $w_{i+1}$.

In some embodiments, the plurality of primary adherence values are combined to calculate the primary composite adherence value using the equation:

$$\sum_{i=1}^{Q} w_i a_i$$

where each $a_i$ is a respective primary adherence value in the plurality of primary adherence values, each $a_i$ occurs in time before and $w_i$ is a weighting factor that is computed as a nonlinear function of time such that $w_i$ is less than $w_{i+1}$.

In some embodiments, each metabolic event in the plurality of metabolic events is a fasting event and the prescribed insulin medicament dosage regimen is a basal insulin medicament dosage regimen.

In some embodiment, the weighted average is calculated as the primary composite adherence value divided by the sum of all weights:

$$\Sigma_{i=1}^{Q} w_i a_i / \Sigma_{i=1}^{Q} w_i.$$

In some embodiments, each metabolic event in the plurality of metabolic events is a meal event, and the prescribed insulin medicament dosage regimen is a bolus insulin medicament dosage regimen.

In some embodiments, the primary single representation is coloured from a colour palette based on a value of the primary composite adherence value.

In some embodiments, the method further comprises binning each respective metabolic event in the plurality of metabolic events on the basis of a plurality of nonoverlapping consecutive secondary time windows within the first period of time. In such embodiments, each respective nonoverlapping consecutive secondary time window is of a same second fixed duration other than the first fixed duration. Further, each respective metabolic event in the plurality of metabolic events is placed into a single nonoverlapping secondary consecutive time window in the plurality of nonoverlapping consecutive secondary time windows when the timestamp for the respective metabolic event is within the single nonoverlapping consecutive secondary time window, thereby obtaining a plurality of secondary subsets of the plurality of metabolic events. Each respective secondary subset of the plurality of metabolic events in the plurality of secondary subsets is for a different secondary time window in the plurality of nonoverlapping consecutive secondary time windows. A plurality of secondary adherence values is then computed, where each respective secondary adherence value in the plurality of secondary adherence values represents a corresponding secondary subset in the plurality of secondary subsets. Each respective secondary adherence value in the plurality of secondary adherence values is computed by dividing a number of insulin regimen adherent metabolic events in the corresponding secondary subset in the plurality of secondary subsets by a total number of metabolic events in the corresponding secondary subset in the plurality of secondary subsets. The plurality of secondary adherence values is then combined into a secondary composite adherence value. The combining downweights a first secondary adherence value, representing a first secondary time window, with respect to a second secondary adherence value, representing a second secondary time window in the plurality of nonoverlapping consecutive secondary time windows, in calculating the secondary composite adherence value, on the basis that the first secondary time window occurs in time before the second secondary time window. The communicating further communicates the secondary composite adherence value as a secondary single representation.

In some embodiments, the method is repeated on a recurring basis over time.

In some embodiments a device (e.g., a portable device) includes a display and the communicating includes presenting the first single representation on the display.

In a further aspect, a second data set is obtained. The second data set comprises a plurality of autonomous glucose measurements of the subject and, for each respective autonomous glucose measurement in the plurality of autonomous glucose measurements, a timestamp representing when the respective measurement was made.

In a further aspect, the method comprises: obtaining a third data set from one or more insulin pens used by the subject to apply the insulin medicament dosage regimen, the third data set comprises a plurality of insulin medicament records, each insulin medicament record in the plurality of medicament records comprising: (i) a respective insulin medicament injection event including an amount of insulin medicament injected into the subject using a respective insulin pen in the one or more insulin pens and (ii) a corresponding electronic timestamp that is automatically generated by the respective insulin pen upon occurrence of the respective insulin medicament injection event; identifying the plurality of metabolic events using the plurality of autonomous glucose measurements of the subject and the respective timestamps in the second data set; applying a first characterization to each respective metabolic event in the plurality of metabolic events, wherein the first characterization is one of insulin regimen adherent and insulin regimen nonadherent, a respective metabolic event is deemed basal regimen adherent when the second data set includes one or more medicament records that establish, on a temporal and quantitative basis, adherence with the insulin medicament dosage regimen during the respective metabolic event, and a respective metabolic event is deemed insulin regimen nonadherent when the second data set fails to include one or more medicament records that establish, on a temporal and quantitative basis, adherence with the insulin medicament dosage regimen.

In a further aspect, the method comprises: obtaining a third data set from one or more insulin pens used by the subject to apply the insulin medicament dosage regimen, the third data set comprises a plurality of insulin medicament records, each insulin medicament record in the plurality of medicament records comprising: (i) a respective insulin medicament injection event including an amount of insulin medicament injected into the subject using a respective insulin pen in the one or more insulin pens and (ii) a corresponding electronic timestamp that is automatically generated by the respective insulin pen upon occurrence of the respective insulin medicament injection event; identifying the plurality of fasting events using the plurality of autonomous glucose measurements of the subject and the respective timestamps in the second data set; applying the first classification to each respective fasting event in the plurality of fasting events, wherein the first classification is one of insulin regimen adherent and insulin regimen nonadherent, a respective fasting event is deemed basal regimen adherent when the second data set includes one or more medicament records that establish, on a temporal and quantitative basis, adherence with the insulin medicament dosage regimen during the respective fasting event, and a respective fasting event is deemed insulin regimen nonadherent when the second data set fails to include one or more medicament records that establish, on a temporal and quantitative basis, adherence with the insulin medicament dosage regimen during the respective fasting event.

In a further aspect the medicament record further comprises a type of insulin medicament, and wherein, a respective fasting event is deemed insulin regimen adherent when one or more medicament records in the plurality of medicament records further indicates in the third data set, on a type of insulin medicament basis, adherence with the standing insulin medicament dosage regimen during the respective fasting event, and a respective fasting event is deemed insulin regimen nonadherent when the plurality of medicament records in the third data set further fails to indicate adherence, on a type of insulin medicament basis with the insulin medicament dosage regimen during the respective fasting period.

In a further aspect the insulin regimen adherent is defined basal regimen adherent, and insulin regiment nonadherent is defined basal regimen nonadherent.

In a further aspect, the method comprises: obtaining a third data set from one or more insulin pens used by the subject to apply the insulin medicament regimen, the third data set comprises a plurality of insulin medicament records, each insulin medicament record in the plurality of medicament records comprising: (i) a respective insulin medicament injection event including an amount of insulin medicament injected into the subject using a respective insulin pen in the one or more insulin pens and (ii) a corresponding electronic timestamp that is automatically generated by the respective insulin pen upon occurrence of the respective insulin medicament injection event; the method further comprises identifying the plurality of meal events using the plurality of autonomous glucose measurements and the corresponding timestamps in the second data set; applying the first classification to each respective meal event in the plurality of meal events, wherein the first classification is one of insulin regimen adherent and insulin regimen nonadherent, a respective meal event is deemed insulin regimen adherent when one or more medicament records in the plurality of medicament records indicates in the third data set, on a temporal basis, a quantitative basis, adherence with the insulin medicament dosage regimen during the respective meal, and a respective meal is deemed insulin regimen nonadherent when the plurality of medicament records in the third data set fails to indicate adherence, on a temporal basis, and a quantitative basis with the insulin medicament dosage regimen during the respective meal.

In a further aspect the medicament record further comprises a type of insulin medicament, and wherein, a respective meal event is deemed insulin regimen adherent when one or more medicament records in the plurality of medicament records further indicates in the third data set, on a type of insulin medicament basis, adherence with the insulin medicament dosage regimen during the respective meal, and a respective meal is deemed insulin regimen nonadherent when the plurality of medicament records in the third data set further fails to indicate adherence, on a type of insulin medicament basis with the insulin medicament dosage regimen during the respective meal.

In a further aspect the insulin regimen adherent is defined as bolus regimen adherent, and insulin regiment nonadherent is defined as bolus regimen nonadherent.

In a further aspect, the metabolic events are automatically obtained from measurement relating to a body function indicating a metabolic event like chewing or swallowing. Depending on the intensity chewing or swallowing may be an indication of a meal event.

In a further aspect, the metabolic events are inherently timestamped, i.e., the timestamp of the metabolic event is a direct consequence of the occurrence of the metabolic event and the timestamp is acquired in response to this occurrence.

Hereby is provided a system ensuring that adherence is monitored with respect to metabolic events that the subject has engaged in, and as the metabolic event is timestamped there is provided a well defined reference in time, allowing the classification of adherence to utilize the timestamp.

In a further aspect, the timestamp relating to a respective metabolic event is used as a starting point for determining whether the metabolic event is insulin regimen adherent or insulin regimen nonadherent.

In a further aspect, wherein the metabolic events are fasting event, the fasting events are identified using the autonomous timestamped glucose measurements of the subject.

In a further aspect, wherein the metabolic events are meal events, the meal events are identified using the autonomous timestamped glucose measurements.

In a further aspect, metabolic events can be a metabolic event defined in the medicament regimen, which can be automatically identified from a device continuously measuring an indicator of an event relating to a metabolic state of the subject, whereby the device allows the metabolic event to be timestamped and to be classified with respect to the medicament regimen as regimen adherent or regimen nonadherent. For example, a metabolic event defined according to the medicament regimen could be a meal event, wherein the medicament regimen determines that bolus insulin should be administered based on glucose measurements relating to this event, or it could be a fasting event, wherein the medicament regimen determines that basal insulin should be administered based on glucose measurements relating to this event.

In another aspect of the present disclosure, a computer program is provided comprising instructions that, when executed by one or more processors, perform a method comprising:
  obtaining a first data set, the first data set comprising a plurality of metabolic events the subject engaged in over an evaluation period, wherein each respective metabolic event in the plurality of metabolic events comprises (i) a timestamp of the respective metabolic event and (ii) a classification that is at least one of insulin regimen adherent and insulin regimen nonadherent;
  binning each respective metabolic event in the plurality of metabolic events on the basis of a plurality of nonoverlapping consecutive primary time windows within the evaluation period, wherein
    each respective nonoverlapping consecutive primary time window in the plurality of nonoverlapping consecutive primary time windows is of a same first fixed duration, and
    each respective metabolic event in the plurality of metabolic events is placed into a single respective nonoverlapping consecutive primary time window in the plurality of nonoverlapping consecutive time windows when the timestamp for the respective metabolic event is within the respective nonoverlapping consecutive primary time window, thereby obtaining a plurality of primary subsets of the plurality of metabolic events, wherein each respective primary subset of the plurality of metabolic events in the plurality of primary subsets is for a different respective nonoverlapping consecutive primary time window in the plurality of nonoverlapping consecutive primary time windows;

computing a plurality of primary adherence values, wherein
- each respective primary adherence value in the plurality of primary adherence values represents a corresponding primary subset in the plurality of primary subsets, and
- each respective primary adherence value in the plurality of primary adherence values is computed by dividing a number of insulin regimen adherent metabolic events in the corresponding primary subset in the plurality of primary subsets by a total number of metabolic events in the corresponding primary subset in the plurality of primary subsets;

combining the plurality of primary adherence values into a primary composite adherence value, wherein the combining downweights a first primary adherence value in the plurality of primary adherence values, representing a first primary time window in the plurality of nonoverlapping consecutive primary time windows, with respect to a second primary adherence value, representing a second primary time window in the plurality of nonoverlapping consecutive primary time windows, in calculating the primary composite adherence value, on the basis that the first primary time window occurs in time before the second primary time window; and communicating the primary composite adherence value as a primary single representation, thereby evaluating historical adherence to the standing insulin medicament dosage regimen for the subject. The computer program can for example be an application for a portable device like a smartphone.

In a further aspect is provided a computer-readable data carrier having stored thereon the computer program.

BRIEF DESCRIPTION OF THE DRAWINGS

FIGS. 4A, 46, 4C, and 4D collectively provide a flow chart of processes and features of a device for evaluating historical adherence to a prescribed insulin medicament dosage regimen in accordance with various embodiments of the present disclosure.

FIG. 6 illustrates an algorithm for considering metabolic events as periods of time and classifying such periods of time in accordance with an embodiment of the present disclosure.

Like reference numerals refer to corresponding parts throughout the several views of the drawings.

DETAILED DESCRIPTION

Figure 1:
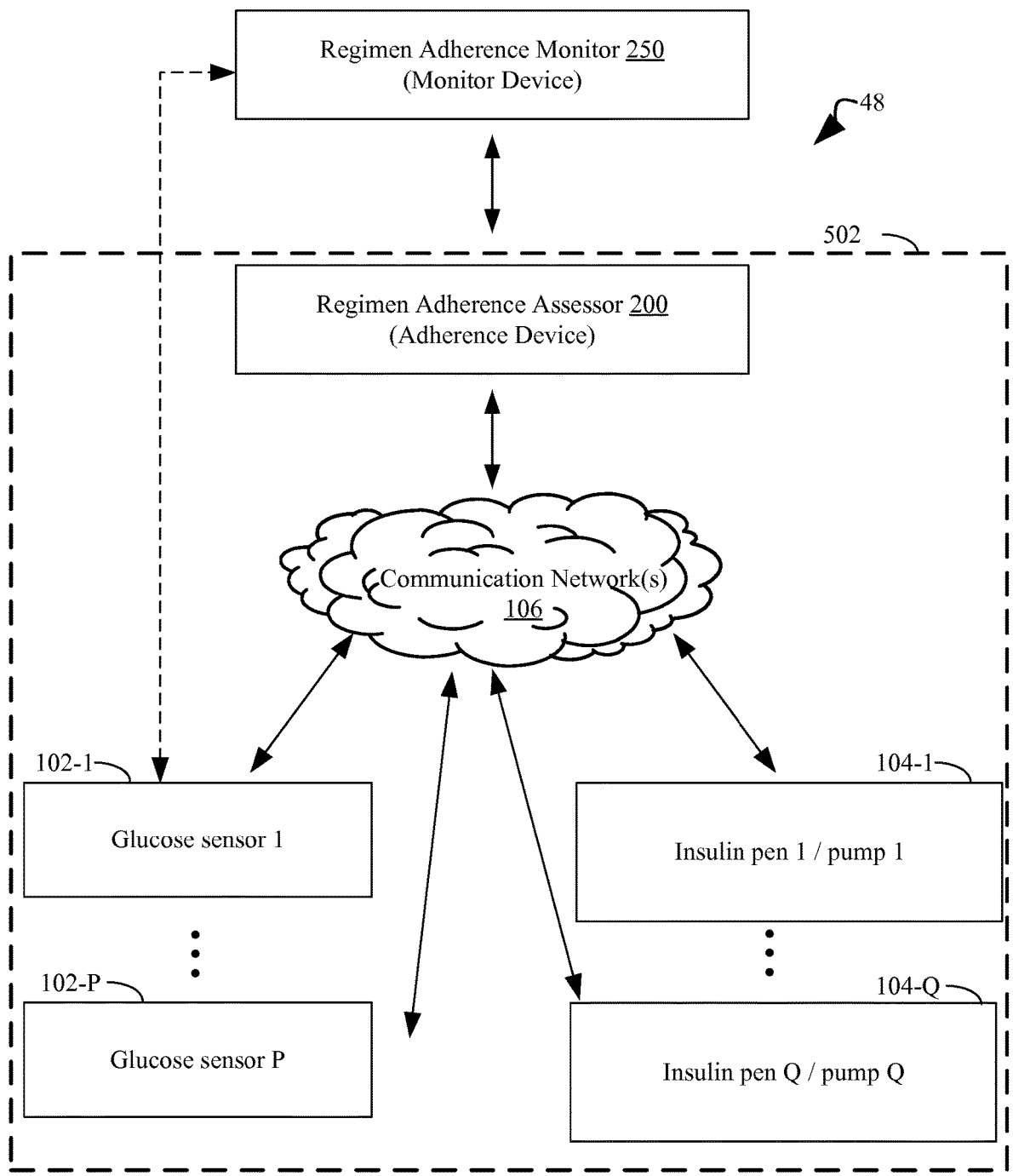
FIG. 1 illustrates an exemplary system topology that includes a regimen adherence monitor device for evaluating historical adherence to a prescribed insulin medicament dosage regimen, a regimen adherence assessor device for analyzing and preparing regimen adherence data, one or more glucose sensors that measure glucose data from the subject, and one or more insulin pens or pumps that are used by the subject to inject insulin medicaments in accordance with the prescribed insulin medicament dosage regimen, where the above-identified components are interconnected, optionally through a communications network, in accordance with an embodiment of the present disclosure.
Figure 5:
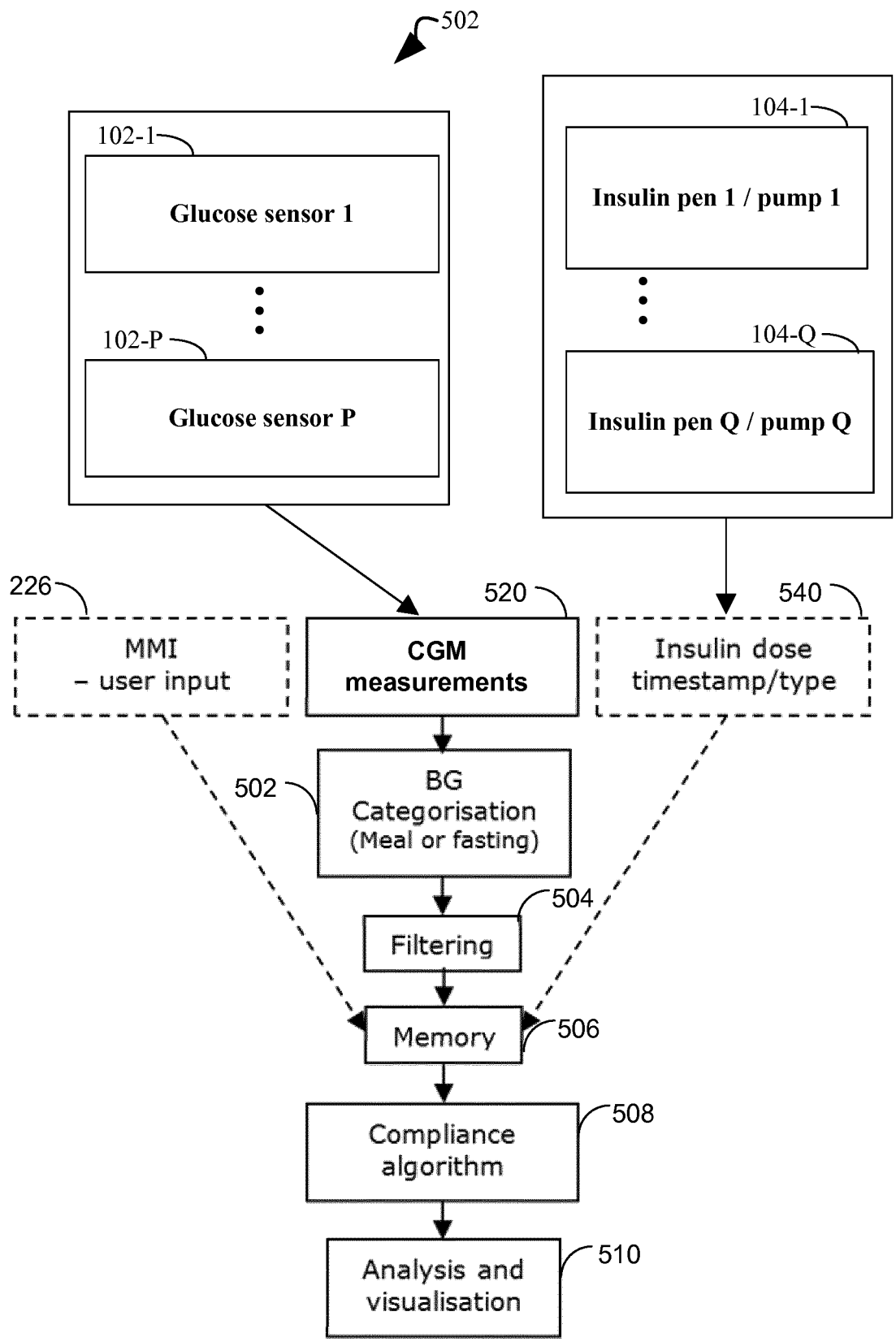
FIG. 5 illustrates an example integrated system of connected insulin pen(s), continuous glucose monitor(s), memory and a processor for performing algorithmic categorization of autonomous glucose data in accordance with an embodiment of the present disclosure.

The present disclosure relies upon the acquisition of data regarding a plurality of metabolic events, such as fasting events or meals, a subject engaged in over a period of time. For each such metabolic event, the data includes a timestamp and a characterization of the metabolic event that is either insulin regimen adherent or insulin regimen nonadherent. FIG. 1 illustrates an example of an integrated system 502 for the acquisition of such data, and FIG. 5 provides more details of such a system 502. The integrated system 502 includes one or more connected insulin pens or pumps 104, one or more continuous glucose monitors 102, memory 506, and a processor (not shown) for performing algorithmic categorization of autonomous glucose data of a subject.

A metabolic event is an event relating to metabolism, which is the sum of the processes in the buildup and destruction of protoplasm, e.g., the chemical changes in living cells by which energy is provided for vital processes and activities and new material is assimilated, i.e., utilized as nourishment.

The metabolism in a living body can be defined in different states: an absorptive state, or fed state, occurs after a meal when the body is digesting food and absorbing nutrients. Digestion begins the moment food enters the mouth, as the food is broken down into its constituent parts to be absorbed through the intestine. The digestion of carbohydrates begins in the mouth, whereas the digestion of proteins and fats begins in the stomach and small intestine. The constituent parts of these carbohydrates, fats, and proteins are transported across the intestinal wall and enter the bloodstream (sugars and amino acids) or the lymphatic system (fats). From the intestines, these systems transport them to the liver, adipose tissue, or muscle cells that will process and use, or store, the energy. In the absorptive state glucose, lipids and amino acids enter the blood stream and insulin may be released (depending on the other conditions like the state and type of diabetes). The postabsorptive state, or the fasting state, occurs when the food has been digested, absorbed, and stored. You commonly fast overnight, but skipping meals during the day puts your body in the postabsorptive state as well. During this state, the body must rely initially on stored glycogen. Glucose levels in the blood begin to drop as it is absorbed and used by the cells. In response to the decrease in glucose, insulin levels also drop. Glycogen and triglyceride storage slows. However, due to the demands of the tissues and organs, blood glucose levels must be maintained in the normal range of 80-120 mg/dL. In response to a drop in blood glucose concentration, the hormone glucagon is released from the alpha cells of the pancreas. Glucagon acts upon the liver cells, where it inhibits the synthesis of glycogen and stimulates the breakdown of stored glycogen back into glucose. This glucose is released from the liver to be used by the peripheral tissues and the brain. As a result, blood glucose levels begin to rise. Gluconeogenesis will also begin in the liver to replace the glucose that has been used by the peripheral tissues. Further information can be found in OpenStax College, Anatomy and Physiology. OpenStax CNX. http://cnx.org/contents/14fb4ad7-39a1-4eee-ab6e-3ef2482e3e22@8.81.

A metabolic event may therefore relate to an event where a certain metabolic state occurs, and the occurrence may be detected by measuring the concentration of an indicator of the event. The metabolic event will be an indicator of the type of state, and the progress of the state, and an indicator of a metabolic event can be the concentration of glucose, glucagon, lipids and amino acids in the blood stream. Other hormones may also be useful for determining events relating to metabolism like cortisol and adrenaline.

Autonomous measurements or autonomous data are measurements or data obtained by a device measuring at a specified or a variable frequency, wherein the measuring is undertaken or carried on without outside control, e.g., when the device is operating in a measurement mode the measuring can be performed without control from the a subject using the device.

With the integrated system 502, autonomous timestamped glucose measurements of the subject are obtained 520. Also, data from the one or more insulin pens and/or pumps used to apply a prescribed insulin regimen to the subject is obtained 540 as a plurality of records. Each record comprises a timestamped event specifying an amount of injected (or pumped) insulin medicament that the subject received as part of the prescribed insulin medicament dosage regimen. Fasting events are identified using the autonomous time-stamped glucose measurements of the subject. Optionally, meal events are also identified using the autonomous time-stamped glucose measurements 502. In this way, the glucose measurements are filtered 504 and stored in non-transitory memory 506.

A metabolic event is characterized as adherent or nonadherent. A metabolic event is adherent when one or more records from the one or more connected insulin pens or pumps 104 temporally and quantitatively establish adherence with the prescribed insulin medicament regimen. Conversely, a metabolic event is characterized as nonadherent when none of the records from the one or more connected insulin pens or pumps 104 temporally and quantitatively establish adherence with the prescribed basal insulin medicament regimen.

Each fasting event is classified as adherent or nonadherent 508. A fasting event is adherent when one or more records from the one or more connected insulin pens or pumps 104 temporally and quantitatively establish adherence with the prescribed basal insulin medicament regimen during the fasting event. Conversely, a fasting event is classified as nonadherent when none of the records from the one or more connected insulin pens or pumps 104 temporally and quantitatively establish adherence with the prescribed basal insulin medicament regimen.

A respective meal is deemed bolus regimen adherent when one or more medicament records indicates, on a temporal basis, a quantitative basis and a type of insulin medicament basis, adherence with a prescribed bolus insulin medicament dosage regimen during the respective meal. Conversely, a respective meal is deemed bolus regimen nonadherent when the plurality of medicament records fails to indicate adherence, on a temporal basis, a quantitative basis, and a type of insulin medicament basis, with the prescribed bolus insulin medicament dosage regimen during the respective meal.

This filtered and cataloged glucose data is analyzed and visualized in accordance with the methods of the present disclosure 510. Such visualization enables the subject or health care practitioner to see the effect of insulin regimen adherence on critical subject markers such as blood glucose levels and HbA1c levels.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject" and "user" are used interchangeably herein. By the term insulin pen is meant an injection device suitable for applying discrete doses of insulin, and wherein the injection device is adapted for logging and communicating dose related data.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Figure 2:
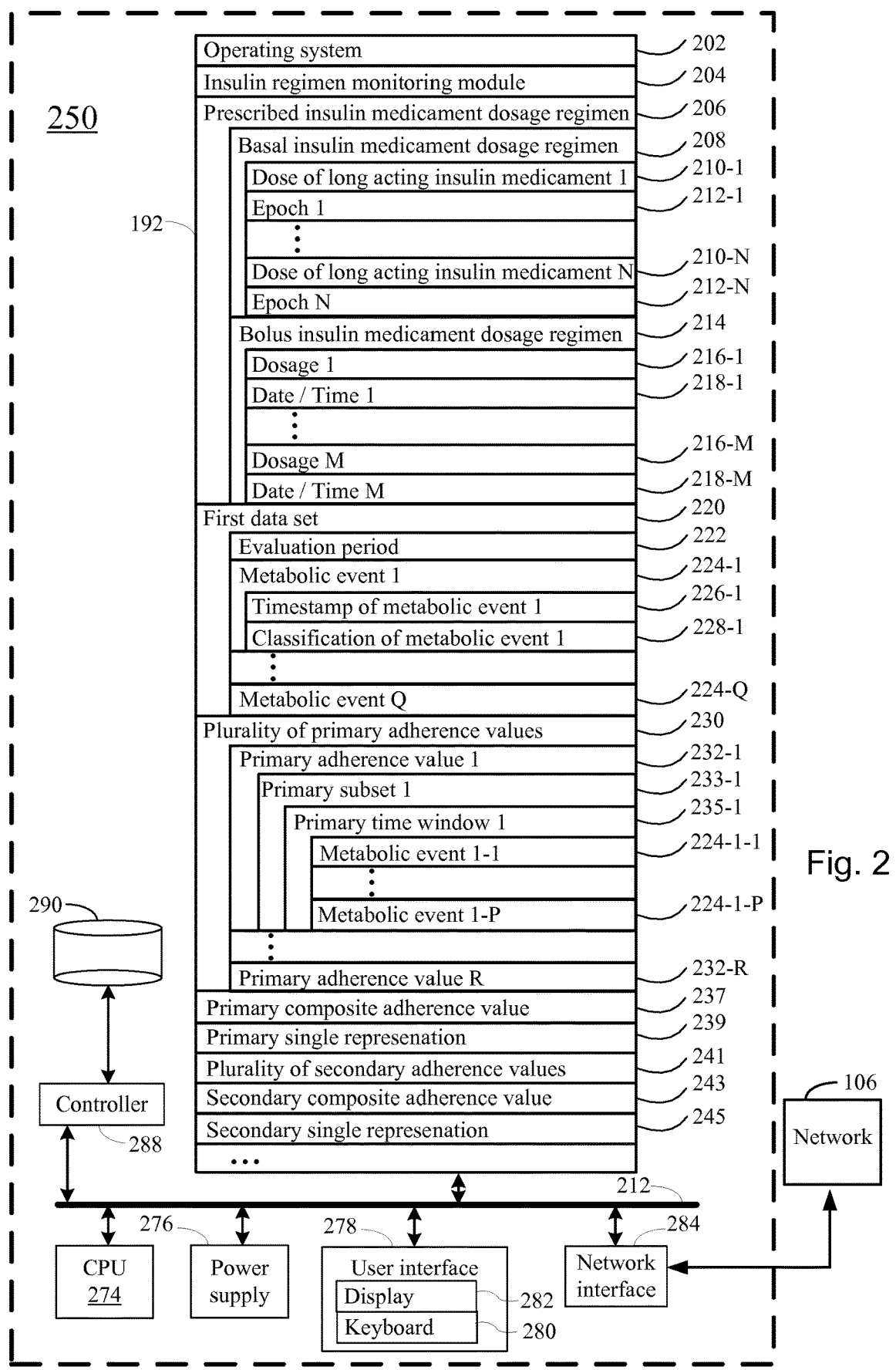
FIG. 2 illustrates a device for evaluating historical adherence to a prescribed insulin medicament dosage regimen in accordance with an embodiment of the present disclosure.
Figure 3:
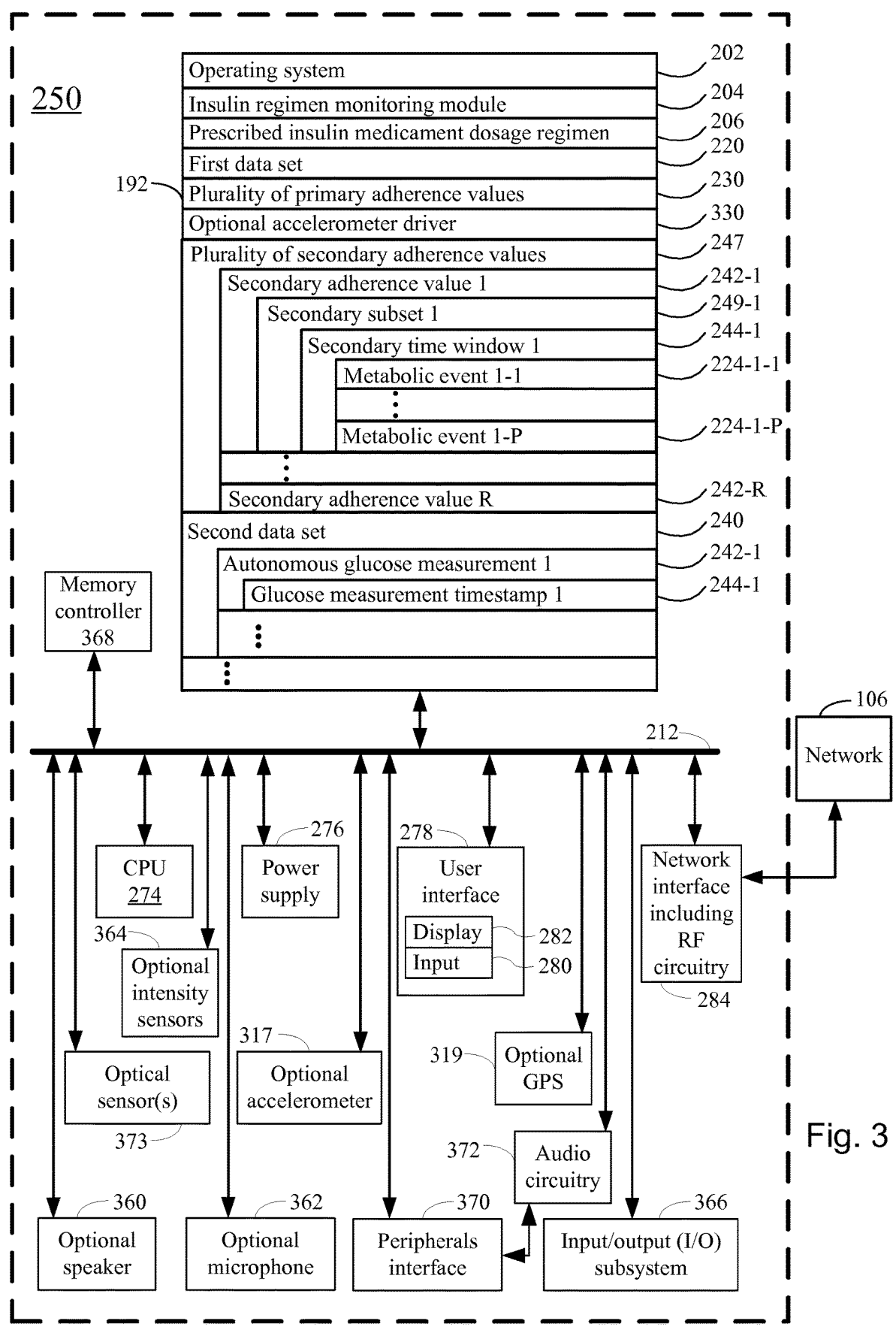
FIG. 3 illustrates a device for evaluating historical adherence to a prescribed insulin medicament dosage regimen in accordance with another embodiment of the present disclosure.

A detailed description of a system 48 for monitoring adherence to a prescribed insulin medicament dosage regimen 206 for a subject over time in accordance with the present disclosure is described in conjunction with FIGS. 1 through 3. As such, FIGS. 1 through 3 collectively illustrate the topology of the system in accordance with the present disclosure. In the topology, there is a device for monitoring adherence to a prescribed insulin medicament dosage regimen ("monitor device 250") (FIGS. 1, 2, and 3), a device for assessing regimen adherence ("adherence device 200"), one or more glucose sensors 102 associated with the subject (FIG. 1), and one or more insulin pens or pumps 104 for injecting insulin medicaments into the subject (FIG. 1). Throughout the present disclosure, the adherence device 200 and the monitor device 250 will be referenced as separate devices solely for purposes of clarity. That is, the disclosed functionality of the adherence device 200 and the disclosed functionality of the monitor device 250 are contained in separate devices as illustrated in FIG. 1. However, it will be appreciated that, in fact, in some embodiments, the disclosed functionality of the adherence device 200 and the disclosed functionality of the monitor device 250 are contained in a single device. In some embodiments, the disclosed functionality of the adherence device 200 and/or the disclosed functionality of the monitor device 250 are contained in a single device and this single device is a glucose monitor 102 or the insulin pump or pen 104.

Referring to FIG. 1, the monitor device 250 monitors adherence to an insulin medicament dosage regimen prescribed to a subject. To do this, the adherence device 200, which is in electrical communication with the monitor device 250, receives autonomous glucose measurements originating from one or more glucose sensors 102 attached to a subject on an ongoing basis. Further, the adherence device 200 receives insulin medicament injection data from one or more insulin pens and/or pumps 104 used by the subject to inject insulin medicaments. In some embodiments, the adherence device 200 receives such data directly from the glucose sensor(s) 102 and insulin pens and/or pumps 104 used by the subject. For instance, in some embodiments the adherence device 200 receives this data wirelessly through radio-frequency signals. In some embodiments such signals are in accordance with an 802.11 (WiFi), Bluetooth, or ZigBee standard. In some embodiments, the adherence device 200 receives such data directly, characterizes or classifies metabolic events within the data as regimen adherent or regimen nonadherent, and passes the classified data to the monitor device 250. In some embodiments the glucose sensor 102 and/or insulin pen/pump includes and RFID tag and communicates to adherence device 200 and/or the monitor device 250 using RFID communication.

In some embodiments, the adherence device 200 and/or the monitor device 250 is not proximate to the subject and/or does not have wireless capabilities or such wireless capabilities are not used for the purpose of acquiring glucose data and insulin medicament injection data. In such embodiments, a communication network 106 may be used to communicate glucose measurements from the glucose sensor 102 to the adherence device 200 and from the one or more insulin pens or pumps 104 to the adherence device 200.

Examples of networks 106 include, but are not limited to, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

In some embodiments, there is a single glucose sensor 102 attached to the subject and the adherence device 200 and/or the monitor device 250 is part of the glucose sensor 102. That is, in some embodiments, the adherence device 200 and/or the monitor device 250 and the glucose sensor 102 are a single device.

In some embodiments, the adherence device 200 and/or the monitor device 250 is part of an insulin pen or pump 104. That is, in some embodiments, the adherence device 200 and/or the monitor device 250 and an insulin pen or pump 104 are a single device.

Of course, other topologies of system 48 are possible. For instance, rather than relying on a communications network 106, the one or more glucose sensors 102 and the one or more insulin pens and/or pumps 104 may wirelessly transmit information directly to the adherence device 200 and/or monitor device 250. Further, the adherence device 200 and/or the monitor device 250 may constitute a portable electronic device, a server computer, or in fact constitute several computers that are linked together in a network or be a virtual machine in a cloud computing context. As such, the exemplary topology shown in FIG. 1 merely serves to describe the features of an embodiment of the present disclosure in a manner that will be readily understood to one of skill in the art.

Referring to FIG. 2, in typical embodiments, the monitor device 250 comprises one or more computers. For purposes of illustration in FIG. 2, the monitor device 250 is represented as a single computer that includes all of the functionality for evaluating historical adherence to a prescribed insulin medicament dosage regimen for a subject. However, the disclosure is not so limited. In some embodiments, the functionality for evaluating historical adherence to a prescribed insulin medicament dosage regimen for a subject is spread across any number of networked computers and/or resides on each of several networked computers and/or is hosted on one or more virtual machines at a remote location accessible across the communications network 106. One of skill in the art will appreciate that any of a wide array of different computer topologies are used for the application and all such topologies are within the scope of the present disclosure.

Turning to FIG. 2 with the foregoing in mind, an exemplary monitor device 250 for evaluating historical adherence to a prescribed insulin medicament dosage regimen for a subject comprises one or more processing units (CPU's) 274, a network or other communications interface 284, a memory 192 (e.g., random access memory), one or more magnetic disk storage and/or persistent devices 290 optionally accessed by one or more controllers 288, one or more communication busses 212 for interconnecting the aforementioned components, and a power supply 276 for powering the aforementioned components. In some embodiments, data in memory 192 is seamlessly shared with non-volatile memory 290 using known computing techniques such as caching. In some embodiments, memory 192 and/or memory 290 includes mass storage that is remotely located with respect to the central processing unit(s) 274. In other words, some data stored in memory 192 and/or memory 290 may in fact be hosted on computers that are external to the monitor device 250 but that can be electronically accessed by the monitor device 250 over an Internet, intranet, or other form of network or electronic cable (illustrated as element 106 in FIG. 2) using network interface 284.

The memory 192 of the monitor device 250 for evaluating historical adherence to a prescribed insulin medicament dosage regimen for a subject stores:
- an operating system 202 that includes procedures for handling various basic system services;
- an insulin regimen monitoring module 204;
- a prescribed insulin medicament dosage regimen 206 for a subject, the prescribed insulin medicament dosage regimen comprising a basal insulin medicament dosage regimen 208 and, optionally in some embodiments, a bolus insulin medicament dosage regimen 214;
- a first data set 220, the first data set representing an evaluation period 222 and comprising a plurality of metabolic events the subject engaged in during this evaluation period and, for each respective metabolic event 224 in the plurality of metabolic events, a timestamp 226 representing when the respective metabolic event occurred as well as a classification 228 of the respective metabolic event;
- a plurality of primary adherence values 230 for the subject, each respective primary adherence value 232 in the plurality of primary adherence values corresponding to a primary subset 233 having a consecutive primary time window 235 within the evaluation period;
- a primary composite adherence value 237 that represents a combination of the plurality of primary adherence values 230;
- a primary single representation 239 of the primary composite adherence value 237;
- an optional plurality of secondary adherence values 241 for the subject, each respective secondary adherence value in the plurality of secondary adherence values corresponding to a secondary subset having a secondary consecutive time window within the evaluation period;
- an optional secondary composite adherence value 243 that represents a combination of the plurality of secondary adherence values; and
- an optional secondary single representation 245 of the secondary composite adherence value 243;

In some embodiments, the insulin regimen monitoring module 204 is accessible within any browser (phone, tablet, laptop/desktop). In some embodiments the insulin regimen monitoring module 204 runs on native device frameworks, and is available for download onto the monitor device 250 running an operating system 202 such as Android or iOS.

In some implementations, one or more of the above identified data elements or modules of the monitor device 250 for evaluating historical adherence to a prescribed insulin medicament dosage regimen for a subject are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 192 and/or 290 optionally stores a subset of the modules and data structures identified above. Furthermore, in some embodiments the memory 192 and/or 290 stores additional modules and data structures not described above.

In some embodiments, a monitor device 250 for evaluating historical adherence to a prescribed insulin medicament dosage regimen for a subject is a smart phone (e.g., an iPHONE), laptop, tablet computer, desktop computer, or other form of electronic device (e.g., a gaming console). In some embodiments, the monitor device 250 is not mobile. In some embodiments, the monitor device 250 is mobile.

FIG. 3 provides a further description of a specific embodiment of a monitor device 250 that can be used with the instant disclosure. The monitor device 250 illustrated in FIG. 3 has one or more processing units (CPU's) 274, peripherals interface 370, memory controller 368, a network or other communications interface 284, a memory 192 (e.g., random access memory), a user interface 278, the user interface 278 including a display 282 and input 280 (e.g., keyboard, keypad, touch screen), an optional accelerometer 317, an optional GPS 319, optional audio circuitry 372, an optional speaker 360, an optional microphone 362, one or more optional intensity sensors 364 for detecting intensity of contacts on the monitor device 250 (e.g., a touch-sensitive surface such as a touch-sensitive display system 282 of the monitor device 250), an optional input/output (I/O) subsystem 366, one or more optional optical sensors 373, one or more communication busses 212 for interconnecting the aforementioned components, and a power supply 276 for powering the aforementioned components.

In some embodiments, the input 280 is a touch-sensitive display, such as a touch-sensitive surface. In some embodiments, the user interface 278 includes one or more soft keyboard embodiments. The soft keyboard embodiments may include standard (QWERTY) and/or non-standard configurations of symbols on the displayed icons.

The monitor device 250 illustrated in FIG. 3 optionally includes, in addition to accelerometer(s) 317, a magnetometer (not shown) and a GPS 319 (or GLONASS or other global navigation system) receiver for obtaining information concerning the location and orientation (e.g., portrait or landscape) of the monitor device 250 and/or for determining an amount of physical exertion by the subject.

It should be appreciated that the monitor device 250 illustrated in FIG. 3 is only one example of a multifunction device that may be used for evaluating historical adherence to a prescribed insulin medicament dosage regimen for a subject, and that the monitor device 250 optionally has more or fewer components than shown, optionally combines two or more components, or optionally has a different configuration or arrangement of the components. The various components shown in FIG. 3 are implemented in hardware, software, firmware, or a combination thereof, including one or more signal processing and/or application specific integrated circuits.

Memory 192 of the monitor device 250 illustrated in FIG. 3 optionally includes high-speed random access memory and optionally also includes non-volatile memory, such as one or more magnetic disk storage devices, flash memory devices, or other non-volatile solid-state memory devices. Access to memory 192 by other components of the monitor device 250, such as CPU(s) 274 is, optionally, controlled by the memory controller 368.

The peripherals interface 370 can be used to couple input and output peripherals of the device to CPU(s) 274 and memory 192. The one or more processors 274 run or execute various software programs and/or sets of instructions stored in memory 192, such as the insulin regimen monitoring module 204, to perform various functions for the monitoring device 250 and to process data.

In some embodiments, the peripherals interface 370, CPU(s) 274, and memory controller 368 are, optionally, implemented on a single chip. In some other embodiments, they are, optionally, implemented on separate chips.

RF (radio frequency) circuitry of network interface 284 receives and sends RF signals, also called electromagnetic signals. In some embodiments, the prescribed insulin medicament dosage regimen 206, the first data set 220, and/or the second data set 240 is received using this RF circuitry from one or more devices such as a glucose sensor 102 associated with a subject, an insulin pen or pump 104 associated with the subject and/or the adherence device 200. In some embodiments, the RF circuitry 108 converts electrical signals to/from electromagnetic signals and communicates with communications networks and other communications devices, glucose sensors 102, and insulin pens or pumps 104 and/or the adherence device 200 via the electromagnetic signals. RF circuitry 284 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 284 optionally communicates with the communication network 106. In some embodiments, the circuitry 284 does not include RF circuitry and, in fact, is connected to the network 106 through one or more hard wires (e.g., an optical cable, a coaxial cable, or the like).

In some embodiments, audio circuitry 372, optional speaker 360, and optional microphone 362 provide an audio interface between the subject and the monitor device 250. The audio circuitry 372 receives audio data from peripherals interface 370, converts the audio data to electrical signals, and transmits the electrical signals to speaker 360. Speaker 360 converts the electrical signals to human-audible sound waves. Audio circuitry 372 also receives electrical signals converted by the microphone 362 from sound waves. Audio circuitry 372 converts the electrical signal to audio data and transmits the audio data to peripherals interface 370 for processing. Audio data is, optionally, retrieved from and/or transmitted to memory 192 and/or RF circuitry 284 by peripherals interface 370.

In some embodiments, the power supply 276 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

In some embodiments, the monitor device 250 optionally also includes one or more optical sensors 373. The optical sensor(s) 373 optionally include charge-coupled device (CCD) or complementary metal-oxide semiconductor (CMOS) phototransistors. The optical sensor(s) 373 receive light from the environment, projected through one or more lens, and converts the light to data representing an image. The optical sensor(s) 373 optionally capture still images and/or video. In some embodiments, an optical sensor is located on the back of the monitor device 250, opposite the display 282 on the front of the device 250, so that the input 280 is enabled for use as a viewfinder for still and/or video image acquisition. In some embodiments, another optical sensor 373 is located on the front of the monitor device 250 so that the subject's image is obtained (e.g., to verify the health or condition of the subject, to determine the physical activity level of the subject, or to help diagnose a subject's condition remotely, etc.).

As illustrated in FIG. 3, a monitor device 250 preferably comprises an operating system 202 that includes procedures for handling various basic system services. The operating system 202 (e.g., iOS, DARWIN, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

In some embodiments the monitor device 250 is a smart phone. In other embodiments, the monitor device 250 is not a smart phone but rather is a tablet computer, desktop computer, emergency vehicle computer, or other form or wired or wireless networked device. In some embodiments, the monitor device 250 has any or all of the circuitry, hardware components, and software components found in the monitor device 250 depicted in FIG. 2 or 3. In the interest of brevity and clarity, only a few of the possible components of the monitor device 250 are shown in order to better emphasize the additional software modules that are installed on the monitor device 250.

While the system 48 disclosed in FIG. 1 can work standalone, in some embodiments it can also be linked with electronic medical records to exchange information in any way.

Now that details of a system 48 for evaluating historical adherence to a prescribed insulin medicament dosage regimen 206 for a subject have been disclosed, details regarding a flow chart of processes and features of the system, in accordance with an embodiment of the present disclosure, are disclosed with reference to FIGS. 4A through 4D. In some embodiments, such processes and features of the system are carried out by the insulin regimen monitoring module 204 illustrated in FIGS. 2 and 3.

Block 402.

With reference to block 402 of FIG. 4A, the goal of insulin therapy in subjects with either type 1 diabetes mellitus or type 2 diabetes mellitus is to match as closely as possible normal physiologic insulin secretion to control fasting and postprandial plasma glucose. This is done with a prescribed insulin medicament dosage regimen 206 for the subject. One aspect of the present disclosure provides a monitoring device 250 for evaluating historical adherence to a prescribed insulin medicament dosage regimen for a subject. In the present disclosure, the prescribed insulin medicament dosage regimen comprises a basal insulin medicament dosage regimen 208. The monitoring device comprises one or more processors 274 and a memory 192/290. The memory stores instructions that, when executed by the one or more processors, perform a method. In the method, a first data set 220 is obtained.

The first data set comprises a plurality of metabolic events in which the subject engaged. The plurality of metabolic events is within a first period of time, referred to herein as evaluation period 222. In varying embodiments, the evaluation period 222 is one day or more, three days or more, five days or more, ten days or more, one month or more, two months or more, three months or more or five months or more. Each respective metabolic event 224 in the plurality of metabolic events comprises (i) a timestamp 226 of the respective metabolic event and (ii) a classification 228 that is one of insulin regimen adherent and insulin regimen nonadherent.

In some embodiments each metabolic event 224 in the first data set 220 has one or more classifications 228 set forth in Table 1.

TABLE 1

Exemplary classifications 228 of metabolic events 224.

| Category A | |
|---|---|
| A1 | In Bolus Adherence |
| A2 | Out of Bolus Adherence |
| Category B | |
| B1 | In Basal Adherence |
| B2 | Out of Basal Adherence |
| Category C | |
| C1 | In timing adherence |
| C2 | Out of timing adherence |
| Category D | |
| D1 | In size adherence |
| D2 | Out of size adherence |

Using the classifications set forth in Table 1, the same period of time can contain metabolic events with different labels. For instance, a whole day can contain a metabolic event (fasting event) marked as out of basal adherence, B2, but three metabolic events (meal events) within that day can be labelled in bolus adherence, A1. FIG. 6 illustrates an algorithm for classifying or marking a metabolic event, wherein the example is a fasting event, and wherein the relevant period of time defined by the regimes is one day. The classification is provided in accordance with the categories of Table 1. In such embodiments, continuously marked periods, e.g. a day, contains a fasting event marked with B2 or a a meal event marked with A1, are referred to as classified metabolic events. As another example, consider the case where three fasting events within each of the first three days of a period of one week are marked as in 100% basal adherence (e.g. basal and timing adherence B1, C1), two fasting events within each of the two following days as in 50% basal adherence (e.g. in basal adherence but out of timing adherence B1, C2), and two fasting event within the last two days as in 0% basal adherence (out of basal adherence and out of timing adherence B2, C2). In the example where a fasting event is classified and marked as in basal and timing adherence the event can as an example be defined as 100% insulin regimen adherent, in the case where the metabolic event is marked in basal adherence, but out of timing adherence the event can as an example be defined as 50% insulin regimen adherent, this could be a different percentage, based on estimated effect of taking a dose later than recommended. In the case where the fasting event is out of basal adherence the event is 0% insulin regimen adherent corresponding to insulin regimen nonadherent. The number of insulin regimen adherent metabolic events in the example is thus 3+2*50%+2*0%. In this example the past week's adherence (primary adherence value 232 for the primary time window 234 of the past week) is thus:

$$\text{Past 7 days' adherence} = \frac{3 + 0.5 * 2}{7} = \frac{4}{7} = 57\%$$

In other embodiments, such classifications are imposed by considering metabolic events to be fasting events or meal events and classifying each fasting event or meal event for insulin medicament regimen adherence.

In some embodiments, metabolic events can be a metabolic events defined in the medicament regimen, which can be automatically identified from a device continuously measuring an indicator of an event, wherein the event is relating to a metabolic state of the subject, whereby the device allows the metabolic event to be timestamped and to be classified with respect to the medicament regimen as regimen adherent or regimen nonadherent. For example, a metabolic event defined according to the medicament regimen could be a meal event, wherein the medicament regimen determines that bolus insulin should be administered based on glucose measurements relating to this event, or it could be a fasting event, wherein the medicament regimen determines that basal insulin should be administered based on glucose measurements relating to this event.

In some embodiments, metabolic events (e.g., meal events, fasting events, etc.) incurred by the subject are identified without reliance on records kept by the subject. For instance, in some embodiments a second data set 240 comprising autonomous glucose measurements 242 of the subject from one or more glucose sensors 102 is obtained. FIG. 3 illustrates. each such autonomous glucose measurement 242 is timestamped with a glucose measurement timestamp 244 to represent when the respective measurement was made.

The FREESTYLE LIBRE CGM by ABBOTT ("LIBRE") is an example of a glucose sensor that may be used as a glucose sensor 102. The LIBRE allows calibration-free glucose measurements with an on-skin coin-sized sensor, which can send up to eight hours of data to a reader device (e.g., the adherence device 200 and/or the monitor device 250) via near field communications, when brought close together. The LIBRE can be worn for fourteen days in all daily life activities. In some embodiments, autonomous glucose measurements are taken from the subject at an interval rate of 5 minutes or less, 3 minutes or less, or 1 minute or less. Example 1 below illustrate how such autonomous glucose measurements are used to both identify metabolic events and to classify each of them as insulin regimen adherent or insulin regimen nonadherent in order to populate the classification 228 of metabolic events 224 in the first data set 220.

Referring to block 404 of FIG. 4A, in some embodiments, each metabolic event in the plurality of metabolic events is a fasting event and the prescribed insulin medicament dosage regimen is a basal insulin medicament dosage regimen. Referring to block 406 of FIG. 4A, in some embodiments, each metabolic event in the plurality of metabolic events is a meal event, and the prescribed insulin medicament dosage regimen is a bolus insulin medicament dosage regimen.
Block 408.

Figure 7:
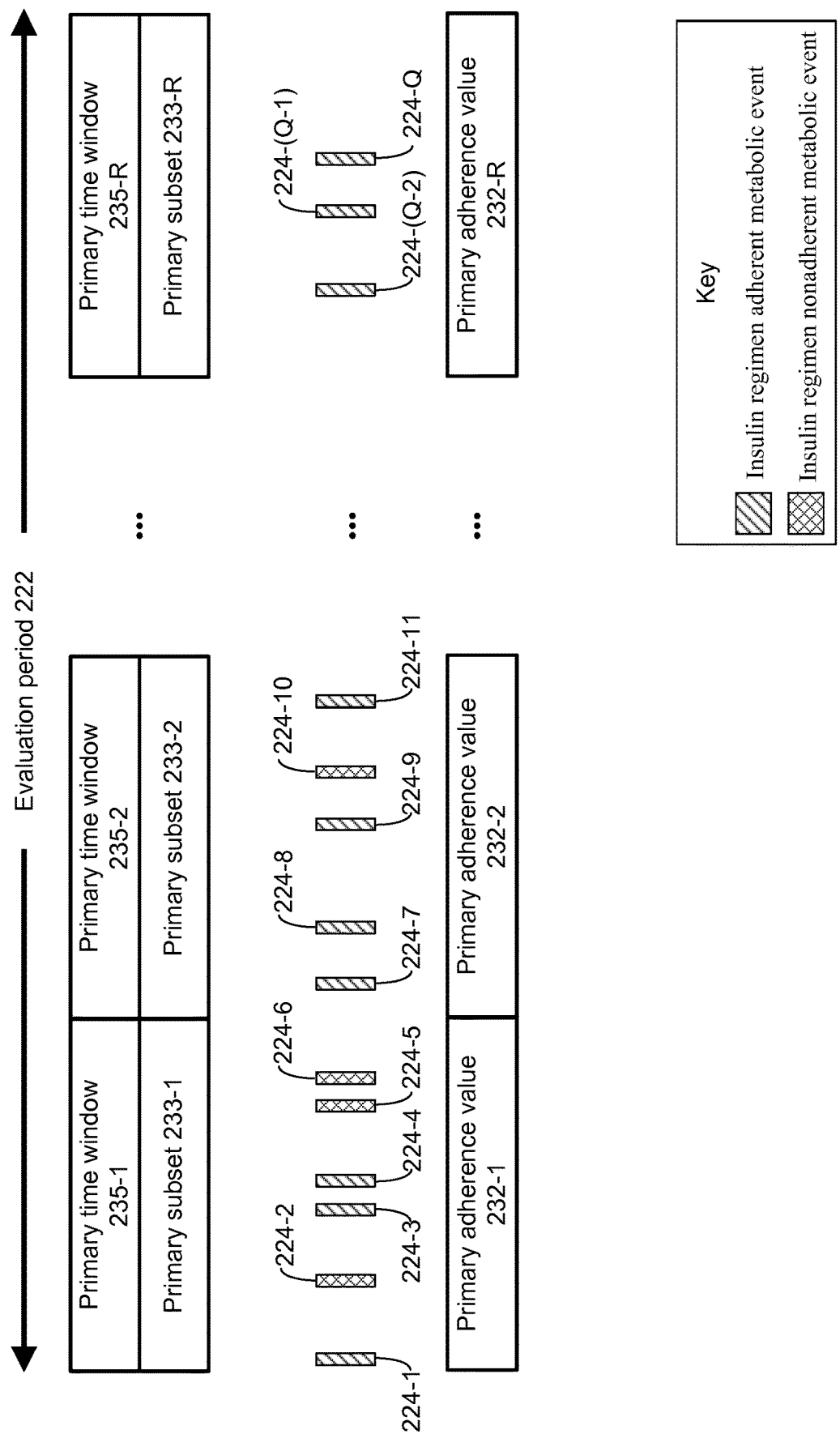
FIG. 7 illustrates computing a plurality of primary adherence values in accordance with an embodiment of the present disclosure.

Referring to block 408 of FIG. 4A, the process continues with the binning of each respective metabolic event 224 in the plurality of metabolic events on the basis of a plurality of nonoverlapping consecutive primary time windows within the evaluation period 222. FIG. 7 illustrates. Each respective nonoverlapping consecutive primary time window 235 in the plurality of nonoverlapping consecutive primary time windows is of a same first fixed duration (e.g., a number of hours, a day, a week, two weeks, or a month, as illustrated in block 410). In FIG. 7, the evaluation period 222 is illustrated as a timeline. Each primary time window 235 is allocated an equal portion of this timeline.

Each respective metabolic event 224 in the plurality of metabolic events of the first data set 220 is placed into a single respective nonoverlapping (temporally consecutive) primary time window 235 in the plurality of nonoverlapping consecutive time windows when the timestamp 226 for the respective metabolic event 224 is within the respective nonoverlapping consecutive primary time window 235, thereby obtaining a plurality of primary subsets of the plurality of metabolic events. Each respective primary subset 233 of the plurality of primary metabolic events in the plurality of primary subsets is for a different respective nonoverlapping consecutive primary time window 235 in the plurality of nonoverlapping consecutive primary time windows.
Block 412.

Referring to block 412 of FIG. 4A and continuing to use FIG. 7 to illustrate, the process continues with the computation of a plurality of primary adherence values 230. Each respective primary adherence value 232 in the plurality of primary adherence values 230 represents a corresponding primary time window 235 in the plurality of primary time windows within the evaluation period 222.

Each respective primary adherence value 232 in the plurality of primary adherence values 230 is computed by dividing a number of insulin regimen adherent metabolic events in the corresponding primary subset 233 by a total number of metabolic events in the corresponding primary subset 233. For example, consider the primary subset 233-1 of FIG. 7 in which there are three insulin regimen adherent metabolic events (224-1, 224-3, and 224-4) and three insulin regimen nonadherent metabolic events (224-2, 224-5, and 224-6) for a total of six metabolic events 224 for the primary subset 233-1. In this example, the primary adherence value 232-1 is computed by dividing the number of insulin regimen adherent metabolic events in the primary subset 231-1 (three, 224-1, 224-3 and 224-4) by the total number of metabolic events in the primary subset 233-1 (six, 224-1, 224-2, 224-3, 224-4, 224-5 and 224-6), that is dividing "3" by "6." It will be appreciated that the process of dividing a number of insulin regimen adherent metabolic events by a total number of metabolic events in a primary subset 233 can be done any number of ways and all such ways are encompassed in the present disclosure. For instance, the division can be effectuated by, in fact, multiplying a number of insulin regimen adherent metabolic events in the primary subset by the inverse of the total number of metabolic events in the primary subset 233 (e.g., in the example above, by computing (3*(⅙)).
Block 414.

Referring to block 414 of FIG. 46, the process continues by combining the plurality of primary adherence values 233 computed above into a primary composite adherence value 237. For instance, referring to FIG. 7, the primary adherence values 232-1 through 232-R are combined to form a primary composite adherence value 237. In block 414, primary adherence values 232 representing earlier primary time windows are downweighted relative to primary adherence values 232 representing later primary time windows. This is done to emphasize more recent metabolic events, which have greater significance in evaluating the historical adherence to a prescribed insulin medicament dosage regimen because they represent more current adherence behavior of the subject. Thus, the combining downweights a first primary adherence value in the plurality of primary adherence values, representing a first primary time window in the plurality of nonoverlapping consecutive primary time windows, with respect to a second primary adherence value, representing a second primary time window in the plurality of nonoverlapping consecutive primary time windows, in calculating the primary composite adherence value, on the basis that the first primary time window occurs in time before the second primary time window. For example, in one embodiment and using FIG. 7 to illustrate, when combining the plurality of primary adherence values into a primary composite adherence value, a first weight is applied against primary adherence value 232-1, a second weight is applied against primary adherence value 232-2 where the first weight is less than the second weight. In this way, the first primary adherence value 232-1 contributes less to the primary composite adherence value 237 than the second primary adherence value 232-2.

There are a number of different ways in which the plurality of primary adherence values can be combined into a primary composite adherence value 237. For instance, referring to block 416 of FIG. 46, in some embodiments, the plurality of primary adherence values are combined into a primary composite adherence value 237 using the formula:

$$\sum_{i=1}^{Q} w_i a_i$$

where, $$\{w_1, \ldots, w_Q\} = \left\{\frac{1}{Q}, \ldots, \frac{Q}{Q}\right\},$$

each $a_i$ is a primary adherence value 237 in the plurality of primary adherence values and occurs in time before a subsequent primary adherence value $a_{i+1}$ (e.g., primary adherence values 232-1 ($a_i$) and 232-2 ($a_{i+i}$) of FIG. 7), and each $w_i$ is an independent weight for a corresponding $a_i$.

In another example, referring to block 418 of FIG. 46, in some embodiments, the plurality of primary adherence values are combined into a primary composite adherence value 237 using the formula:

$$\sum_{i=1}^{Q} w_i a_i$$

where, each $a_i$ is a primary adherence value 232 in the plurality of primary adherence values and occurs in time before a subsequent primary adherence value $a_{i+1}$ (e.g., primary adherence values 232-1 ($a_i$) and 232-2 ($a_{i+i}$) of FIG. 7), each $w_i$ is an independent weight for a corresponding $a_i$, each $w_i$ is (i) equal to a first value when $w_i$ represents a primary time window that is before a threshold time and (ii) equal to a second value when $w_i$ represents a primary time window that is after the threshold time, and the first value is smaller than the second value.

Figure 8:
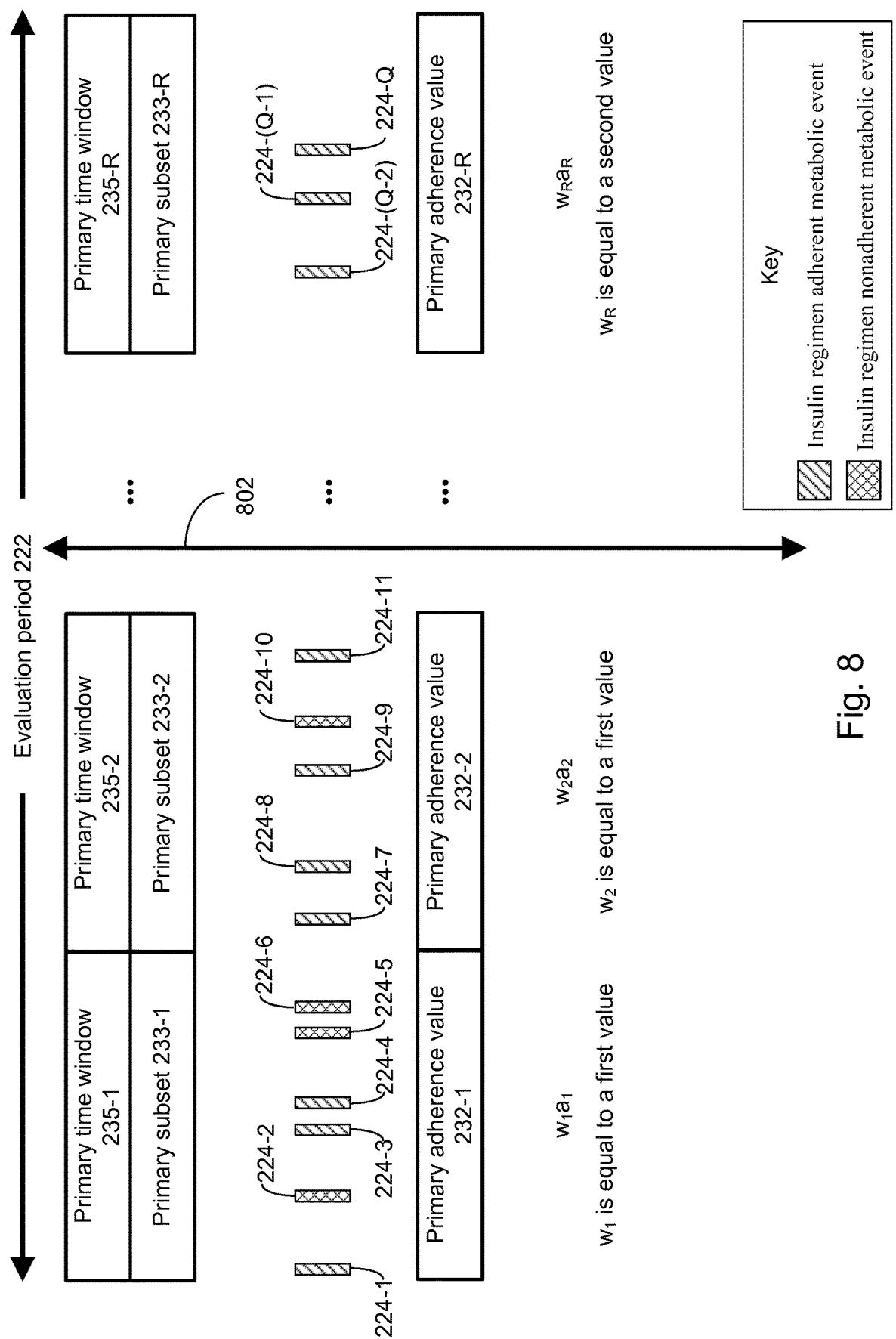
FIG. 8 illustrates combining a plurality of primary adherence values into a primary composite adherence value, where the combining downweights a first primary adherence value in a plurality of primary adherence values, representing a first primary time window, with respect to a second primary adherence value, representing a second primary time window, in calculating a primary composite adherence value, on the basis that the first primary time window occurs in time before the second primary time window, in accordance with embodiment of the present disclosure.

FIG. 8 illustrates such an embodiment. Each primary adherence value 232 ($a_i$) is multiplied by a corresponding weight to form the set $\{w_1 a_1, w_2 a_2, \ldots, w_R a_R\}$ and this set is summed to form the primary composite adherence value 237. The weight $w_i$ of those primary adherence values 232 that occur before the threshold time represented by the line 802 in FIG. 8 are each equal to a first value and those primary adherence values 232 that occur after the threshold time 802 are each equal to a second value.

Referring to block 420 of FIG. 46 and using FIG. 8 to illustrate, in some embodiment the threshold time 802 is two weeks prior to when the combining is performed, four weeks prior to when the combining is performed, or six weeks prior to when the combining is performed. In other words, in some embodiments, the primary adherence values 232 formed using the metabolic events occurring more than two weeks ago, more than four weeks ago, or more than six weeks ago are each weighted against a first weight whereas primary adherence values 232 formed using more recent metabolic events (after the threshold time 802) are each weighted against a second weight. In still other words, in some embodiments the primary adherence values 232 formed using the metabolic events occurring more than two weeks ago, more than four weeks ago, or more than six weeks ago are each down-weighted whereas primary adherence values 232 formed using more recent metabolic events (after the threshold time 802) are relatively up-weighted. In some such embodiments, the first value is zero and the second value is 1. Thus, to illustrate using FIG. 8, the weight $w_i$ of those primary adherence values 232 that occur before the threshold time represented by the line 802 in FIG. 8 do not contribute to the primary composite adherence value 237 whereas those primary adherence values 232 that occur after the threshold time 802 do contribute to the primary composite adherence value 237.

Figure 4C:
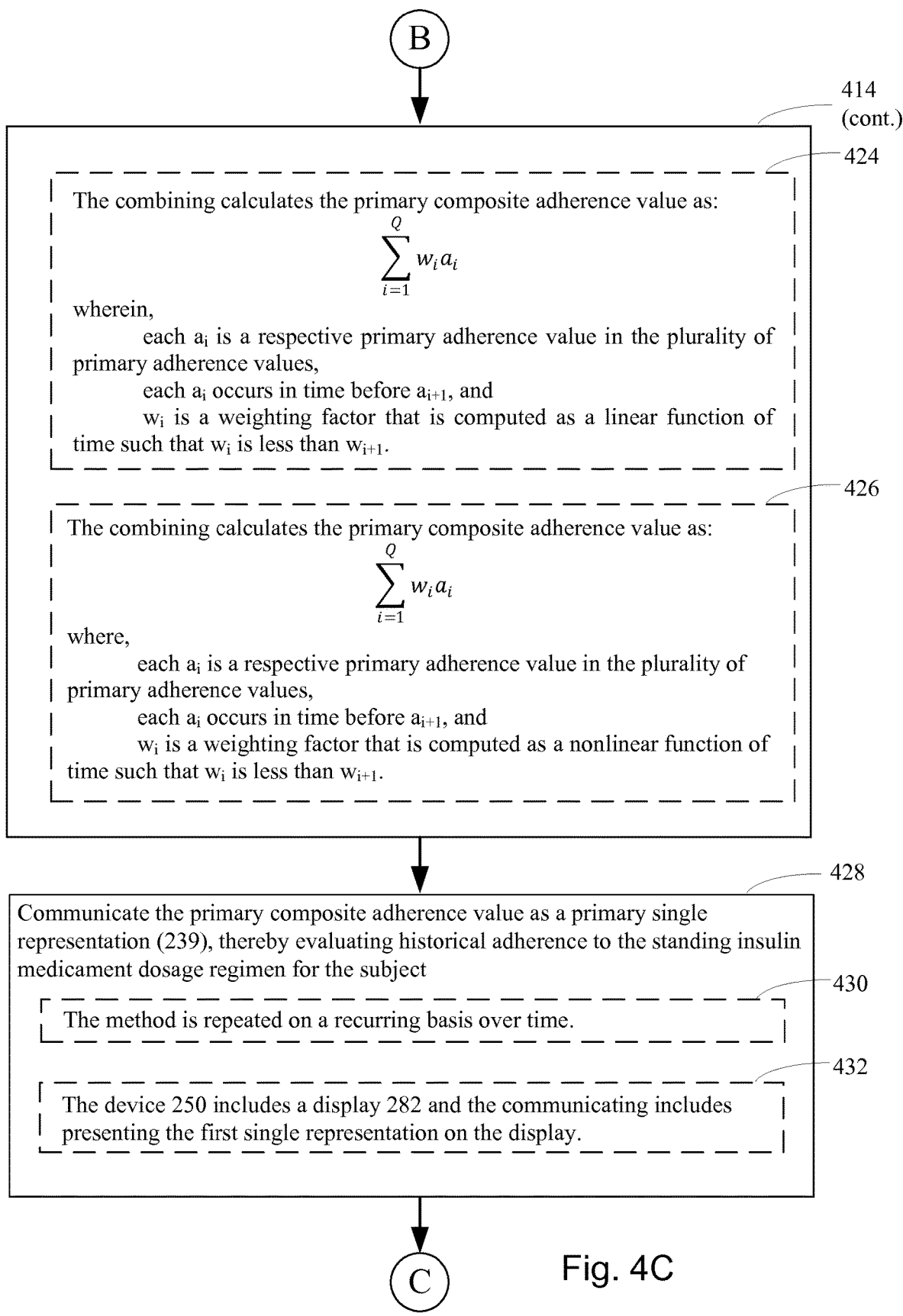

In another example, referring to block 424 of FIG. 4C, in some embodiments, the plurality of primary adherence values are combined into a primary composite adherence value 237 using the formula:

$$\sum_{i=1}^{Q} w_i a_i$$

where,
each $a_i$ is a respective primary adherence 232 value in the plurality of primary adherence values,
each $a_i$ occurs in time before $a_{i+1}$, and
$w_i$ is a weighting factor that is computed as a linear function of time such that $w_i$ is less than $w_{i+1}$.

Figure 9:
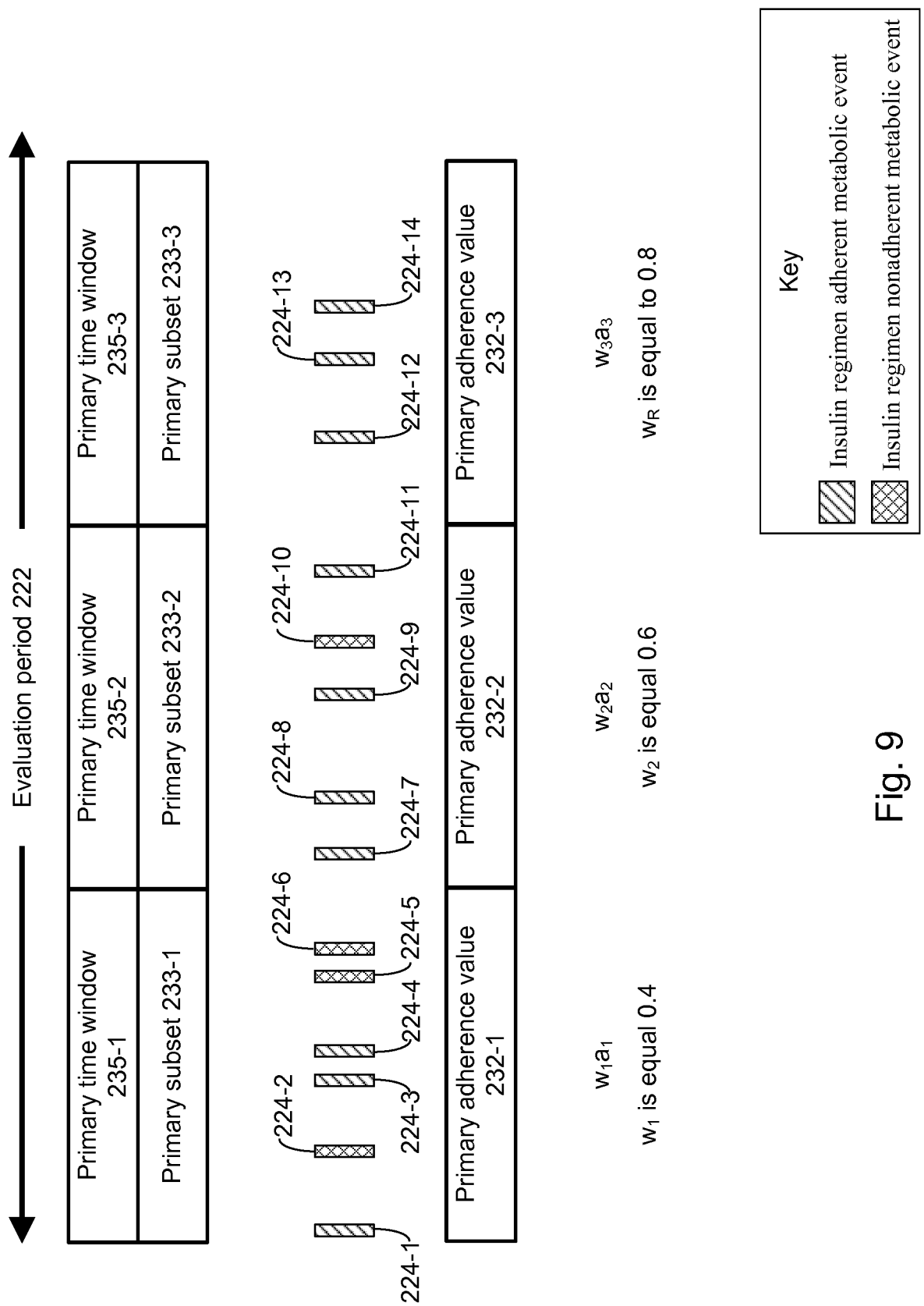
FIG. 9 illustrates combining a plurality of primary adherence values into a primary composite adherence value in accordance with another embodiment of the present disclosure.

For instance, referring to FIG. 9 to illustrate, an example of a linear function of time is to dampen $w_i$ as a function of the age of the primary time window 235 corresponding to the primary adherence value 232. For purposes of this example, the age of a time window 235 is deemed to be the endpoint of the time window in the evaluation period 222. Thus, the primary time window 235-3 is one week old when the primary composite adherence value 237 is combined, and so the corresponding primary adherence value 232-3 receives a weight $w_3$ of 0.8, the primary time window 235-2 is two weeks old when the primary composite adherence value 237 is combined, and so the corresponding primary adherence value 232-2 receives a weight $w_2$ of 0.6, the primary time window 235-1 is three weeks old when the primary composite adherence value 237 is combined, and so the corresponding primary adherence value 232-1 receives a weight $w_1$ of 0.4.

In another example, referring to block 426 of FIG. 4C, in some embodiments, the plurality of primary adherence values are combined into a primary composite adherence value 237 using the formula:

$$\sum_{i=1}^{Q} w_i a_i$$

where,
each $a_i$ is a respective primary adherence value in the plurality of primary adherence values,
each $a_i$ occurs in time before and
$w_i$ is a weighting factor that is computed as a nonlinear function of time such that $w_i$ is less than $w_{i+1}$.

An example of a nonlinear function of time is that provided in FIG. 8 in which each primary adherence value 232 ($a_i$) is multiplied by a corresponding weight to form the set $\{w_1 a_1, w_2 a_2, \ldots, w_R a_R\}$ and this set is summed to form the primary composite adherence value 237. The weight $w_i$ of those primary adherence values 232 that occur before the threshold time represented by the line 802 in FIG. 8 are each equal to a first value and those primary adherence values 232 that occur after the threshold time 802 are each equal to a second value, where the first value is other than the second value.

In some embodiments, the plurality of primary adherence values are combined into a primary composite adherence value by taking a weighted average of the plurality of primary adherence values or a measure of central tendency of the primary adherence values. This measure of central tendency can be, for example, an arithmetic mean, weighted mean, midrange, midhinge, trimean, Winsorized mean, median, or mode of such values. In some embodiments, the plurality of primary adherence values are combined into a primary composite adherence value by taking a weighted average of the of the N most recent primary adherence values or a measure of central tendency of the of the N most recent primary adherence values, where N is a positive integer (e.g., 1, 2, 3, 4, 5, 6, etc.). This measure of central tendency can be, for example, an arithmetic mean, weighted mean, midrange, midhinge, trimean, Winsorized mean, median, or mode of such values.

Block 428.

Figure 10:
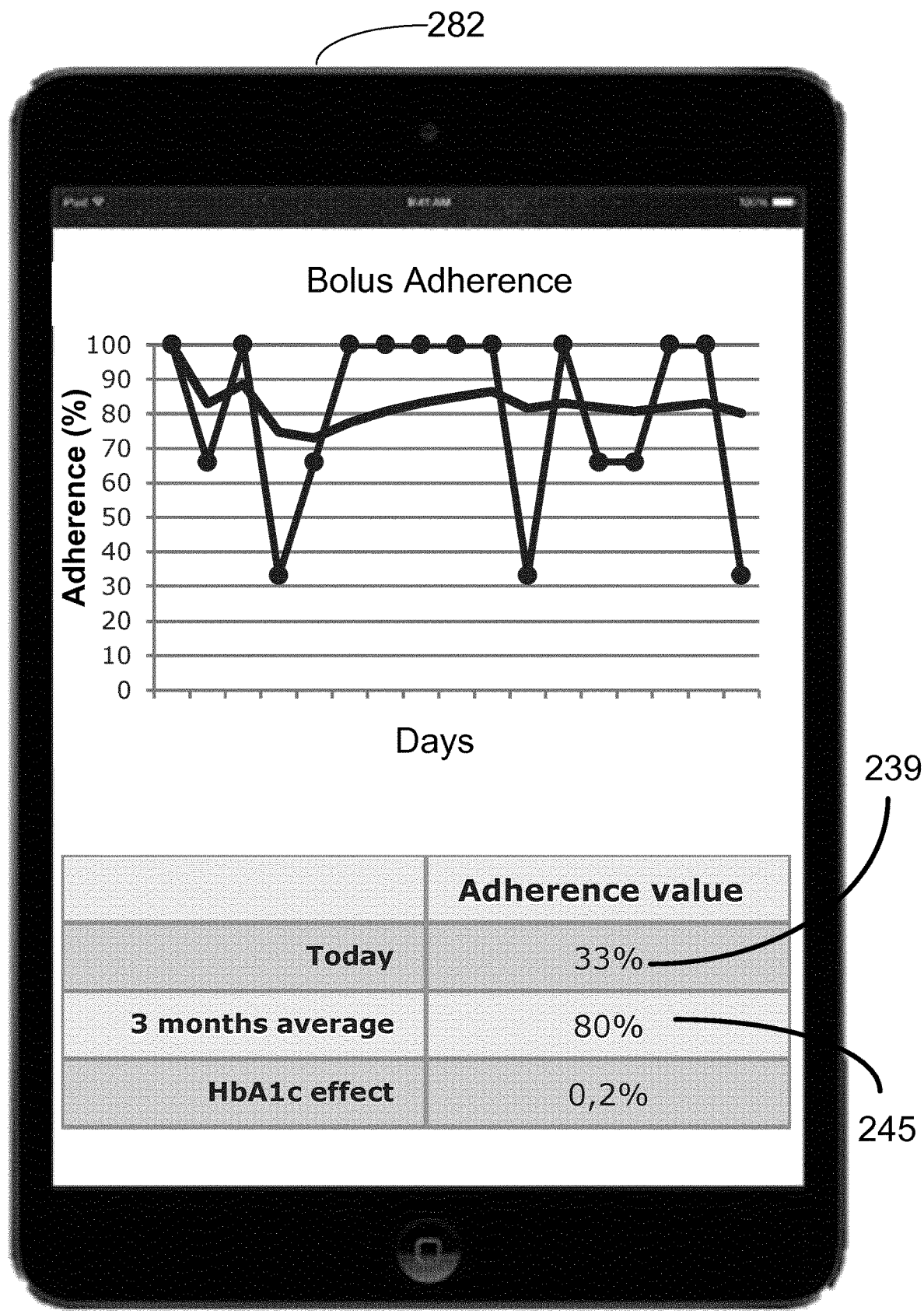
FIG. 10 illustrates communicating a primary composite adherence value as a primary single representation and a secondary composite adherence value as a secondary single representation in accordance with an embodiment of the present disclosure.

Referring to block 428 of FIG. 4C, the primary composite adherence value 237 is communicated as a primary single representation 239, thereby evaluating historical adherence to the standing insulin medicament dosage regimen for the subject. FIG. 10 illustrates. In FIG. 10, the primary composite adherence value 237 is communicated as a primary single representation 239 in the form of a percentile (33%). In other embodiments, the primary composite adherence value 237 is communicated as a primary single representation 239 in the form of colour code (e.g., green is a satisfactory underlying primary composite adherence value 237, yellow is a borderline underlying primary composite adherence value 237, and red is an unhealthy underlying primary composite adherence value 237). For instance, in the illustration of FIG. 10, the percentile is shown in red in some embodiments when the value falls below a predetermined value indicating that the subject's adherence condition is unsatisfactory.

Referring to block 430 of FIG. 4C, the disclosed method is repeated on a recurring basis over time in order to keep the primary composite adherence value 237 continually updated with fresh data in the first data set. That is, in typical embodiments, the first data set 220 is dynamic in nature, meaning that new classified metabolic events are received over time, and these are used to update the primary composite adherence value 237 in accordance with the disclosed systems and methods.

Referring to block 430 of FIG. 4C, in some embodiments, the device 250 includes a display 282 and the communicating includes presenting the first single representation 239 on the display. This is illustrated in FIG. 10, as described above.

Referring to block 432 of FIG. 4D, in some embodiments, a secondary single representation 245 is displayed. For instance, referring to the example of FIG. 10, the primary single representation 239 represents a primary composite adherence value 237 computed using only the metabolic events 224 that occurred in the present day, whereas the secondary single representation 245 represents a secondary composite adherence value 243 computed using the metabolic events 224 over the past three months. As such, the secondary single representation 245, and its underlying secondary composite adherence value 243, differs from the primary single representation 239, and its underlying primary composite adherence value 237, in that the underlying secondary composite adherence value 243 is computed independent of the primary composite adherence value 237. In particular, referring to FIGS. 3, 4C, and 4D, each respective nonoverlapping consecutive secondary time window 244 in the plurality of nonoverlapping consecutive secondary time windows used as the basis for computing the secondary adherence values 242 that are combined to form the secondary composite adherence value 234 (FIG. 4C) are of a same second fixed duration that is other than the first fixed duration of the primary time windows 235 that are used as the basis for computing the primary adherence values 232 that are combined to form the primary composite adherence value 237.

Moreover, when combining the secondary adherence values 242 to form the secondary composite adherence value 243, the secondary adherence values 242 can be weighted using any of the weighting or combination schemes described above for combining the primary adherence values 232 (e.g., a linear or nonlinear weighting of secondary adherence values 242 as a function of time and/or the taking of a measure of central tendency of the secondary adherence values 242) when forming the secondary composite adherence value 243. In fact, in some embodiments, a different weighting scheme is used for combining the primary adherence values 232 than is used for combining the secondary adherence values 242 when respectively combining them to form the respective primary composite adherence value 237 and secondary composite adherence value 243.

Figure 11:
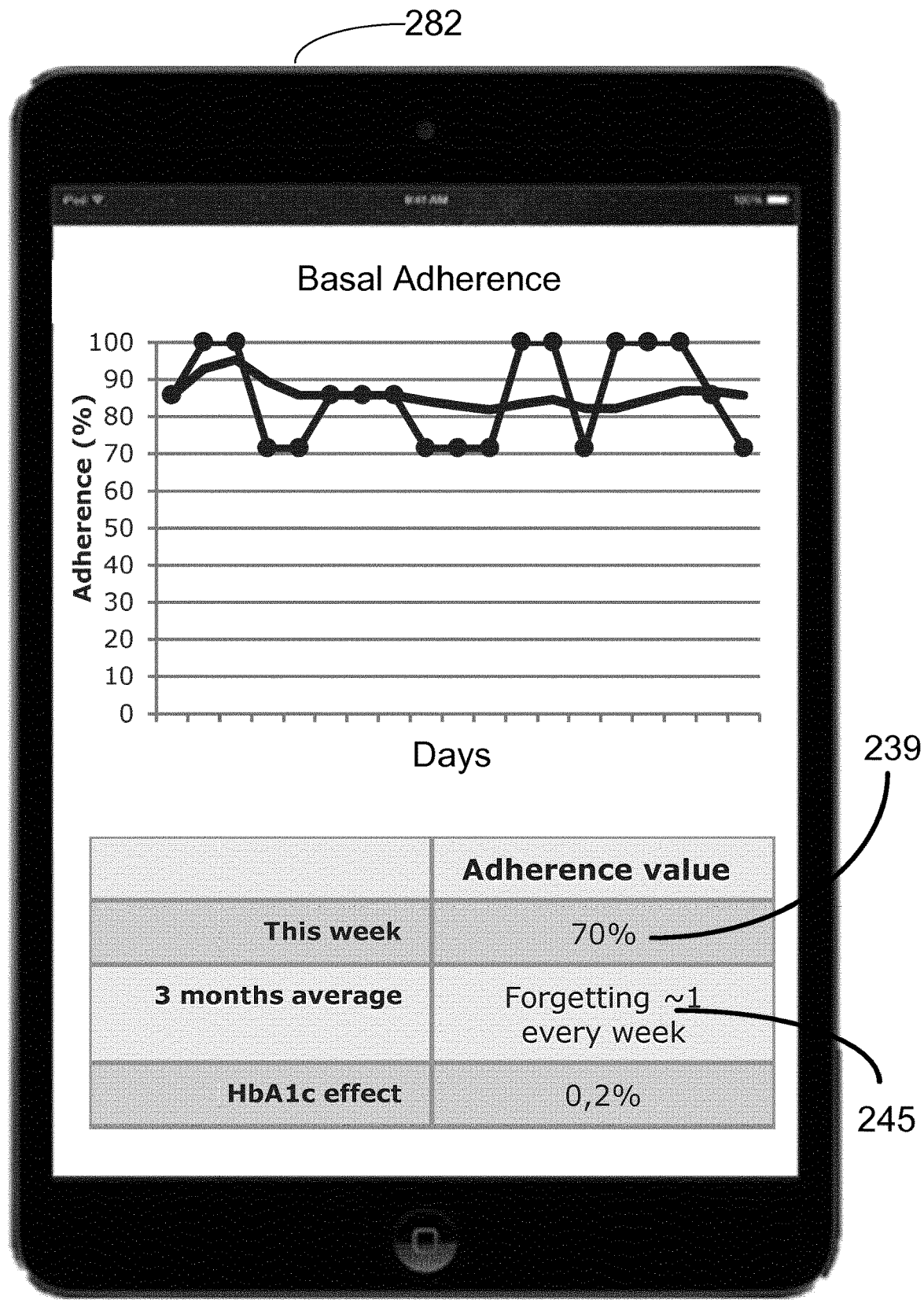
FIG. 11 illustrates communicating a primary composite adherence value as a primary single representation and a secondary composite adherence value as a secondary single representation in accordance with an embodiment of the present disclosure.

While FIG. 10 illustrates communicating a primary composite adherence value 237 as a primary single representation 239 for bolus adherence, FIG. 11 illustrates communicating a primary composite adherence value 237 as a primary single representation 239 for basal adherence.

Throughout the present disclosure, in some embodiments, a secondary single representation 245 is simply the value of the secondary composite adherence value 243. Throughout the present disclosure, in some embodiments, a secondary single representation 245 is an icon, color code, line thickness, or hash mark the represents a value of the secondary composite adherence value 243.

Throughout the present disclosure, in some embodiments, a primary single representation 239 is simply the value of the primary composite adherence value 237. Throughout the present disclosure, in some embodiments, a primary single representation 239 is an icon, color code, line thickness, or hash mark the represents a value of the primary composite adherence value 237.

Example 1: Use of Autonomous Glucose Measurements to Identify Metabolic Events and to Classify them as Insulin Regimen Adherent or Insulin Regimen Nonadherent In some embodiments, a second data set 240 comprising a plurality of glucose measurements is obtained autonomously. In this example, in addition to the autonomous glucose measurements, insulin administration events are obtained in the form of insulin medicament records from one or more insulin pens and/or pumps 104 used by the subject to apply the prescribed insulin regimen. These insulin medicament records may be in any format, and in fact may be spread across multiple files or data structures. As such, in some embodiments, the instant disclosure leverages the recent advances of insulin administration pens, which have become "smart" in the sense that they can remember the timing and the amount of insulin medicament administered in the past. One example of such an insulin pen 104 is the NovoPen 5. Such pens assists patients in logging doses and prevent double dosing. It is contemplated that insulin pens will be able to send and receive insulin medicament dose volume and timing, thus allowing the integration of continuous glucose monitors 102, insulin pens 104 and the algorithms of the present disclosure. As such, insulin medicament records from one or more insulin pens 104 and/or pumps is contemplated, including the wireless acquisition of such data from the one or more insulin pens 104.

In some embodiments, each insulin medicament record comprises: (i) a respective insulin medicament injection event including an amount of insulin medicament injected into the subject using a respective insulin pen in the one or more insulin pens and (ii) a corresponding electronic timestamp that is automatically generated by the respective insulin pen 104 upon occurrence of the respective insulin medicament injection event.

In some embodiments, a plurality of fasting events, which is one form of metabolic event 224, are identified using the autonomous glucose measurements 242 of the subject and their associated glucose measurement timestamps 244 in the second data set 240. Glucose measurements during fasting events are of importance for measuring basal glucose levels.

There are a number of methods for detecting a fasting event using autonomous glucose measurements 242 from a glucose monitor 102. For instance, in some embodiments a first fasting event (in the plurality of fasting events) is identified in a first time period (e.g., a period of 24 hours) encompassed by the plurality of autonomous glucose measurements by first computing a moving period of variance $\sigma_k^2$ across the plurality of autonomous glucose measurements, where:

$$\sigma_k^2 = \left( \frac{1}{M} \sum_{i=k-M}^{k} (G_i - \overline{G}) \right)^2$$

and where, $G_i$ is the $i^{th}$ glucose measurement in the portion k of the plurality of glucose measurements, M is a number of glucose measurements in the plurality of glucose measurements and represents a contiguous predetermined time span, $\overline{G}$ is the mean of the M glucose measurements selected from the plurality of glucose measurements, and k is within the first time period. As an example, the glucose measurements may span several days or weeks, with autonomous glucose measurements taken every five minutes. A first time period k (e.g., one day) within this overall time span is selected and thus the portion k of the plurality of measurements is examined for a period of minimum variance. The first fasting period is deemed to be the period of minimum variance $$\min_{k} \sigma_k^2$$

within the first time period. Next, the process is repeated with portion k of the plurality of glucose measurements by examining the next portion k of the plurality of glucose measurements for another period of minimum variance thereby assigning another fasting period. Repetition of this method through all portions k of the plurality of glucose measurements is used to build the plurality of fasting periods.

Once the fasting events are identified, by the method described above or any other method, a classification 228 is applied to each respective fasting event in the plurality of identified fasting events. Thus, for each respective fasting event there is a classification 228 for the respective fasting event. The classification is one of insulin regimen adherent and insulin regimen nonadherent. More specifically, here, the classification is one of basal insulin regimen adherent and basal insulin regimen nonadherent.

A respective fasting event is deemed basal insulin regimen adherent when the acquired one or more medicament records establish, on a temporal and quantitative basis, adherence with the prescribed basal insulin medicament dosage regimen during the respective fasting event. A respective fasting event is deemed basal regimen nonadherent when the acquired one or more medicament records do not include one or more medicament records that establish, on a temporal and quantitative basis, adherence with the prescribed basal insulin medicament dosage regimen during the respective fasting event. In some embodiments the basal regimen 208 specifies that a basal dose of long acting insulin medicament 210 is to be taken during each respective epoch 212 in a plurality of epochs and that a respective fasting event is deemed basal insulin medicament regimen 208 nonadherent when there are no medicament records for the epoch 212 associated with the respective fasting event. In various embodiments, each epoch in the plurality of epochs is two days or less, one day or less, or 12 hours or less. Thus, consider the case where the second data set 240 is used to identify a fasting period and the prescribed basal insulin medicament dosage regimen 208 specifies to take dosage A of a long acting insulin medicament 210 every 24 hours. In this example, therefore, the epoch is one day (24 hours). The fasting event is inherently timestamped because it is derived from a period of minimum variance in timestamped glucose measurements, or by other forms of analysis of the timestamped autonomous glucose measurements. Thus the timestamp, or period of fasting, represented by a respective fasting event is used as a starting point for examining whether the fasting event is basal insulin medicament regimen adherent. For instance, if the period of fasting associated with the respective timestamp is 6:00 AM on Tuesday, May 17, what is sought in the medicament injection records is evidence that the subject took dosage A of the long acting insulin medicament in the 24 hour period (the epoch) leading up to 6:00 AM on Tuesday, May 17 (and not more or less of the prescribed dosage). If the subject took the prescribed dosage of the long acting insulin medicament during this epoch, the respective fasting event (and/or the basal injection event and/or the glucose measurements during this time) is deemed basal regimen adherent. If the subject did not take the prescribed dosage of the long acting insulin medicament 210 during this epoch 212 (or took more than the prescribed dosage of the long acting insulin medicament during this period), the respective fasting event (and/or the basal injection event and/or the glucose measurements during this time) is deemed basal regimen nonadherent.

While the use of the fasting event to retrospectively determine whether a basal injection event is basal insulin medicament regimen adherent has been described, the present disclosure is not so limited. In some embodiments, the epoch is defined by the basal insulin medicament regimen and, so long as the subject took the amount of basal insulin required by the basal regimen during the epoch (and not more), even if after the fasting event, the fasting event will be deemed basal insulin medicament regimen adherent. For instance, if the epoch is one day beginning each day at just after midnight (in other words the basal regimen specifies one or more basal insulin medicament dosages to be taken each day, and further defines a day as beginning and ending at midnight), and the fasting event occurs at noon, the fasting event will be deemed compliant provided that the subject takes the basal injections prescribed for the day at some point during the day.

In some embodiments a fasting event is not detected during an epoch when, in fact, the basal insulin medicament regimen specifies that a basal insulin injection event must occur. Thus, the basal injection should be taken according to the prescribed basal insulin medicament regimen 208. According to the above use case, this epoch would not have a basal adherence categorization for failure to find a fasting event. In some such embodiments, because the basal insulin medicament dosage regimen 208 is known, a determination as to the adherence (of the glucose measurement during the epoch in question and/or the basal injection event in the epoch) based on the basal insulin medicament regimen itself and the injection event data, and thus does not require detecting the fasting period from the injection event data. As another example, if the basal insulin medicament regimen is once weekly basal injection, the exemplary procedure would look for a basal injection within a seven day window even if a fasting event is not found.

In some embodiments, the prescribed insulin medicament dosage regimen 206 further a bolus insulin medicament dosage regimen 214 in addition to or instead of the basal insulin medicament dosage regimen 208.

In embodiments where the subject is taking more than one insulin medication type, each respective insulin medicament injection event in the plurality of medicament records provides a respective type of insulin medicament injected into the subject from one of (i) a long acting insulin medicament and (ii) a short acting insulin medicament. Typically, the long acting insulin medicament is for a basal insulin medicament dosage regimen 208 whereas the short acting insulin medicament is for a bolus insulin medicament dosage regimen 214.

Thus, advantageously, the instant disclosure can also make use of the bolus insulin medicament injection events, when such events are available, to provide an additional type of categorized metabolic event 224 in the first data set 220. In some such embodiments, the bolus insulin medicament injection events are made use of in the following way. A plurality of meal events are identified using the plurality of autonomous glucose measurements 242 and the corresponding timestamps 244 in the second data set 240 using a meal detection algorithm. If no meal is detected, the process ends. If a meal is detected then a classification is applied to the respective meal event. In this way, a plurality of meal events, with each respective meal event including a classification that is one of "bolus regimen adherent" and "bolus regimen nonadherent" is acquired. Such information can then be used in the systems and methods of the present disclosure, where each meal is considered a metabolic event 224 and the classification of such meals as "bolus regimen adherent" and "bolus regimen nonadherent" is the classification 228 of the metabolic event.

In some embodiments, a respective meal is deemed bolus regimen adherent when one or more medicament records in the plurality of medicament records indicates, on a temporal basis, a quantitative basis and a type of insulin medicament basis, adherence with the bolus insulin medicament dosage regimen 214 during the respective meal. In some embodiments, a respective meal is deemed bolus regimen nonadherent when the plurality of medicament records fails to indicate adherence, on a temporal basis, a quantitative basis, and a type of insulin medicament basis, with the standing bolus insulin medicament dosage regimen during the respective meal. For instance, consider the case where the standing bolus insulin medicament dosage regimen specifies that dosage A of insulin medicament B is to be taken up 30 minutes before a respective meal and that a certain meal that occurred at 7:00 AM on Tuesday, May 17. It will be appreciated that dosage A may be a function of the anticipated size or type of meal. What is sought in the medicament records is evidence that the subject took dosage A of insulin medicament B in the 30 minutes leading up to 7:00 AM on Tuesday, May 17 (and not more or less of the prescribed dosage). If the subject took the prescribed dosage A of the insulin medicament B during the 30 minutes leading up to the respective meal, the respective meal (and/or the bolus administration(s) and/or the glucose measurements during this time) is deemed bolus regimen adherent. If the subject did not take the prescribed dosage A of the insulin medicament B during the 30 minutes leading up to the respective meal (or took more than the prescribed dosage A of the insulin medicament B during this period), the respective meal (and/or the bolus administration and/or the glucose measurements during this time) is deemed bolus regimen nonadherent. The time period of 30 minutes here is exemplary, in other embodiments the time is shorter or longer (e.g., between 15 minutes to 2 hours prior to the meal and/or is dependent upon the type of insulin medicament prescribed). In some embodiments, the bolus regimen permits the bolus injection to be taken a short time after the meal.

In some embodiments, a plurality of feed-forward events are acquired and used to help classify metabolic events. In some embodiments, each respective feed-forward event represents an instance where the subject has indicated they are having or are about to have a meal. In such embodiments, the plurality of meal events determined using the autonomous glucose measurements 242 are verified against the plurality of feed-forward events by either removing any respective meal event in the plurality of meal events that fails to temporally match any feed-forward event in the plurality of feed-forward events.

In some embodiments, the bolus insulin medicament dosage regimen 214 specifies that the short acting insulin medicament is to be taken up to a predetermined amount of time prior to a meal. In some such embodiments, a respective meal is deemed bolus regimen nonadherent when there is no insulin medicament record of the short acting insulin medicament type having an electronic timestamp up to the predetermined amount of time prior to the respective meal. In some such embodiments, the predetermined amount of time is thirty minutes or less, twenty minutes or less, or fifteen minutes or less.

In some embodiments, the long acting insulin medicament consists of a single insulin medicament having a duration of action that is between 12 and 24 hours or a mixture of insulin medicaments that collectively have a duration of action that is between 12 and 24 hours. Examples of such long acting insulin medicaments include, but are not limited to Insulin Degludec (developed by NOVO NORDISK under the brand name Tresiba), NPH (Schmid, 2007, "New options in insulin therapy. J Pediatria (Rio J). 83 (Suppl 5):S146-S155), Glargine (LANTUS, Mar. 2, 2007, insulin glargine [rDNA origin] injection, [prescribing information], Bridgewater, N.J.: Sanofi-Aventis), and Determir (Plank et al., 2005, "A double-blind, randomized, dose-response study investigating the pharmacodynamic and pharmacokinetic properties of the long-acting insulin analog detemir," Diabetes Care 28:1107-1112).

In some embodiments, the short acting insulin medicament consists of a single insulin medicament having a duration of action that is between three to eight hours or a mixture of insulin medicaments that collectively have a duration of action that is between three to eight hours. Examples of such short acting insulin medicaments include, but are not limited, to Lispro (HUMALOG, May 18, 2001, insulin lispro [rDNA origin] injection, [prescribing information], Indianapolis, Ind.: Eli Lilly and Company), Aspart (NOVOLOG, July 2011, insulin aspart [rDNA origin] injection, [prescribing information], Princeton, N.J., NOVO NORDISK Inc., July, 2011), Glulisine (Helms Kelley, 2009, "Insulin glulisine: an evaluation of its pharmacodynamic properties and clinical application," Ann Pharmacother 43:658-668), and Regular (Gerich, 2002, "Novel insulins: expanding options in diabetes management," Am J Med. 113:308-316).

In some embodiments, the identification of the plurality of meal events from the autonomous glucose measurements 242 in the second data set 240 is performed by computing: (i) a first model comprising a backward difference estimate of glucose rate of change using the plurality of autonomous glucose measurements, (ii) a second model comprising a backward difference estimate of glucose rate of change based on Kalman filtered estimates of glucose using the plurality of autonomous glucose measurements, (iii) a third model comprising a Kalman filtered estimate of glucose and Kalman filtered estimate of rate of change (ROC) of glucose based on the plurality of autonomous glucose measurements, and/or (iv) a fourth model comprising a Kalman filtered estimate of rate of change of ROC of glucose based on the plurality of autonomous glucose measurements. In some such embodiments, the first model, the second model, the third model and the fourth model are each computed across the plurality of autonomous glucose measurements and each respective meal event in the plurality of meal events is identified at an instance where at least three of the four models indicate a meal event. For further disclosure on such meal event detection, see Dassau et al., 2008, "Detection of a Meal Using Continuous Glucose Monitoring," Diabetes Care 31, pp. 295-300, which is hereby incorporated by reference. See also, Cameron et al., 2009, "Probabilistic Evolving Meal Detection and Estimation of Meal Total Glucose Appearance," Journal of Diabetes Science and Technology 3(5), pp. 1022-1030, which is hereby incorporated by reference.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a nontransitory computer readable storage medium. For instance, the computer program product could contain the program modules shown in any combination of FIG. 1, 2, or 3 and/or described in FIG. 4. These program modules can be stored on a CD-ROM, DVD, magnetic disk storage product, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

The invention claimed is:

1. A device for evaluating historical adherence to a prescribed insulin medicament dosage regimen for a subject, wherein the device comprises one or more processors and a memory, the memory storing instructions that, when executed by the one or more processors, perform a method of:

obtaining a first data set, the first data set comprising a plurality of metabolic events the subject engaged in over an evaluation period, wherein each respective metabolic event in the plurality of metabolic events comprises (i) a timestamp of the respective metabolic event and (ii) a classification that is at least one of insulin regimen adherent and insulin regimen nonadherent;

binning each respective metabolic event in the plurality of metabolic events on the basis of a plurality of nonoverlapping consecutive primary time windows within the evaluation period, wherein
   each respective nonoverlapping consecutive primary time window in the plurality of nonoverlapping consecutive primary time windows is of a same first fixed duration, and
   each respective metabolic event in the plurality of metabolic events is placed into a single respective nonoverlapping consecutive primary time window in the plurality of nonoverlapping consecutive time windows when the timestamp for the respective metabolic event is within the respective nonoverlapping consecutive primary time window, thereby obtaining a plurality of primary subsets of the plurality of metabolic events, wherein each respective primary subset of the plurality of metabolic events in the plurality of primary subsets is for a different respective nonoverlapping consecutive primary time window in the plurality of nonoverlapping consecutive primary time windows;

computing a plurality of primary adherence values, wherein
   each respective primary adherence value in the plurality of primary adherence values represents a corresponding primary subset in the plurality of primary subsets, and
   each respective primary adherence value in the plurality of primary adherence values is computed by dividing a number of insulin regimen adherent metabolic events in the corresponding primary subset in the plurality of primary subsets by a total number of metabolic events in the corresponding primary subset in the plurality of primary subsets;

obtaining a second data set comprising a plurality of autonomous glucose measurements of the subject and, for each respective autonomous glucose measurement in the plurality of autonomous glucose measurements, a timestamp representing when the respective measurement was made, obtaining a third data set from one or more insulin pens used by the subject to apply the insulin medicament dosage regimen, the third data set comprises a plurality of insulin medicament records, each insulin medicament record in the plurality of medicament records comprising:
(i) a respective insulin medicament injection event including an amount of insulin medicament injected into the subject using a respective insulin pen in the one or more insulin pens, and
(ii) a corresponding electronic timestamp that is automatically generated by the respective insulin pen upon occurrence of the respective insulin medicament injection event,
identifying the plurality of metabolic events using the plurality of autonomous glucose measurements of the subject and the respective timestamps in the second data set, applying a first characterization to each respective metabolic event in the plurality of metabolic events, wherein the first characterization is one of insulin regimen adherent and insulin regimen nonadherent,
wherein:
(i) each metabolic event in the plurality of metabolic events is a fasting event and the prescribed insulin medicament dosage regimen is a basal insulin medicament dosage regimen, a respective metabolic event is deemed basal regimen adherent when the second data set includes one or more medicament records that establish, on a temporal and quantitative basis, adherence with the insulin medicament dosage regimen during the respective metabolic event, and a respective metabolic event is deemed insulin regimen nonadherent when the second data set fails to include one or more medicament records that establish, on a temporal and quantitative basis, adherence with the insulin medicament dosage regimen,
or wherein:
(ii) each metabolic event in the plurality of metabolic events is a meal event, and the prescribed insulin medicament dosage regimen is a bolus insulin medicament dosage regimen, a respective meal event is deemed insulin regimen adherent when one or more medicament records in the plurality of medicament records indicates in the third data set, on a temporal basis, a quantitative basis, adherence with the insulin medicament dosage regimen during the respective meal, and a respective meal is deemed insulin regimen nonadherent when the plurality of medicament records in the third data set fails to indicate adherence, on a temporal basis, and a quantitative basis with the insulin medicament dosage regimen during the respective meal,
combining the plurality of primary adherence values into a primary composite adherence value, wherein the combining downweights a first primary adherence value in the plurality of primary adherence values, representing a first primary time window in the plurality of nonoverlapping consecutive primary time windows, with respect to a second primary adherence value, representing a second primary time window in the plurality of nonoverlapping consecutive primary time windows, in calculating the primary composite adherence value, on the basis that the first primary time window occurs in time before the second primary time window;
generating and communicating the primary composite adherence value as a primary single representation to a display configured to display the primary composite adherence value along with a time period associated with the primary composite adherence value, thereby evaluating historical adherence to the standing insulin medicament dosage regimen for the subject and
causing the display to provide a graphical user interface comprising a representation of the plurality of nonoverlapping consecutive primary time windows extending over at least the time period associated with the primary composite adherence value, each of said plurality of nonoverlapping consecutive primary time windows associated with a primary adherence value in the plurality of primary adherence values, and selectively providing, on the graphical user interface, the primary composite adherence value in an area separated from the representation of the plurality of nonoverlapping consecutive primary time windows.

2. The device of claim 1, wherein the combining calculates the primary composite adherence value as:

$$\sum_{i=1}^{Q} w_i a_i$$

wherein, $$\{w_1, \ldots, w_Q\} = \left\{\frac{1}{Q}, \ldots, \frac{Q}{Q}\right\},$$

each $a_i$ is a primary adherence value in the plurality of primary adherence values and occurs in time before $a_{i+1}$, and
each $w_i$ is an independent weight for a corresponding $a_i$.

3. The device of claim 1, wherein the combining calculates the primary composite adherence value as:

$$\sum_{i=1}^{Q} w_i a_i$$

wherein,
each $a_i$ is a primary adherence value in the plurality of primary adherence values and occurs in time before $a_{i+1}$,
each $w_i$ is an independent weight for a corresponding $a_i$,
each $w_i$ is (i) equal to a first value when wi represents a primary time window that is before a threshold time and (ii) equal to a second value when wi represents a primary time window that is after the threshold time, and
the first value is smaller than the second value
wherein:
each metabolic event in the plurality of metabolic events is a fasting event and the prescribed insulin medicament dosage regimen is a basal insulin medicament dosage regimen; or
each metabolic event in the plurality of metabolic events is a meal event, and
the prescribed insulin medicament dosage regimen is a bolus insulin medicament dosage regimen.

4. The device of claim 3, wherein the threshold time is two weeks prior to when the combining is performed, four weeks prior to when the combining is performed, or six weeks prior to when the combining is performed.

5. The device of claim 3, wherein the first value is zero and the second value is 1.

6. The device of claim 1, wherein the same first fixed duration is a day, a week, two weeks, or a month.

7. The device of claim 1, wherein the primary single representation is coloured from a colour palette based on a value of the primary composite adherence value.

8. The device of claim 1, the method further comprising:
binning each respective metabolic event in the plurality of metabolic events on the basis of a plurality of nonoverlapping consecutive secondary time windows within the first period of time, wherein
each respective nonoverlapping consecutive secondary time window in the plurality of nonoverlapping consecutive secondary time windows is of a same second fixed duration other than the first fixed duration, and
each respective metabolic event in the plurality of metabolic events is placed into a single nonoverlapping secondary consecutive time window in the plurality of nonoverlapping consecutive secondary time windows when the timestamp for the respective metabolic event is within the single nonoverlapping consecutive secondary time window, thereby obtaining a plurality of secondary subsets of the plurality of metabolic events, wherein each respective secondary subset of the plurality of metabolic events in the plurality of secondary subsets is for a different secondary time window in the plurality of nonoverlapping consecutive secondary time windows;
computing a plurality of secondary adherence values, wherein
each respective secondary adherence value in the plurality of secondary adherence values represents a corresponding secondary subset in the plurality of secondary subsets, and
each respective secondary adherence value in the plurality of secondary adherence values is computed by dividing a number of insulin regimen adherent metabolic events in the corresponding secondary subset in the plurality of secondary subsets by a total number of metabolic events in the corresponding secondary subset in the plurality of secondary subsets;
combining the plurality of secondary adherence values into a secondary composite adherence value, wherein the combining downweights a first secondary adherence value in the plurality of secondary adherence values, representing a first secondary time window in the plurality of nonoverlapping consecutive secondary time windows, with respect to a second secondary adherence value, representing a second secondary time window in the plurality of nonoverlapping consecutive secondary time windows, in calculating the secondary composite adherence value, on the basis that the first secondary time window occurs in time before the second secondary time window; and
the communicating further communicates the secondary composite adherence value as a secondary single representation, and further causes the display to provide a graphical user interface element on the graphical user interface comprising the secondary single representation of the secondary composite adherence value, said secondary single representation provided in an area separated from the representation of the plurality of nonoverlapping consecutive primary time windows.

9. The device of claim 1, wherein the method is repeated on a recurring basis over time.

10. The device of claim 1, wherein the device includes a display and the communicating includes presenting the first single representation on the display.

11. The device of claim 1, wherein the combining calculates the primary composite adherence value as:

$$\sum_{i=1}^{Q} w_i a_i$$

wherein,
each $a_i$ is a respective primary adherence value in the plurality of primary adherence values,
each $a_i$ occurs in time before $a_{i+1}$, and
$w_i$ is a weighting factor that is computed as a linear function of time such that $w_i$ is less than $w_{i+1}$.

12. The device of claim 1, wherein the combining calculates the primary composite adherence value as:

$$\sum_{i=1}^{Q} w_i a_i$$

wherein,
each $a_i$ is a respective primary adherence value in the plurality of primary adherence values,
each $a_i$ occurs in time before $a_{i+1}$, and
$w_i$ is a weighting factor that is computed as a nonlinear function of time such that $w_i$ is less than $w_{i+1}$.

13. A method of evaluating historical adherence to a prescribed insulin medicament dosage regimen for a subject, the method comprising:
obtaining a first data set, the first data set comprising a plurality of metabolic events the subject engaged in over an evaluation period, wherein each respective metabolic event in the plurality of metabolic events comprises (i) a timestamp of the respective metabolic event and (ii) a classification that is at least one of insulin regimen adherent and insulin regimen nonadherent;
binning each respective metabolic event in the plurality of metabolic events on the basis of a plurality of nonoverlapping consecutive primary time windows within the evaluation period, wherein
each respective nonoverlapping consecutive primary time window in the plurality of nonoverlapping consecutive primary time windows is of a same first fixed duration, and
each respective metabolic event in the plurality of metabolic events is placed into a single nonoverlapping consecutive primary time window in the plurality of nonoverlapping consecutive primary time windows when the timestamp for the respective metabolic event is within the respective nonoverlapping consecutive primary time window, thereby obtaining a plurality of primary subsets of the plurality of metabolic events, wherein each respective primary subset of the plurality of metabolic events in the plurality of primary subsets is for a different nonoverlapping consecutive primary time window in the plurality of nonoverlapping consecutive primary time windows;

computing a plurality of primary adherence values, wherein
 each respective primary adherence value in the plurality of primary adherence values represents a corresponding primary subset in the plurality of primary subsets, and
 each respective primary adherence value in the plurality of primary adherence values is computed by dividing a number of insulin regimen adherent metabolic events in the corresponding primary subset in the plurality of primary subsets by a total number of metabolic events in the corresponding primary subset in the plurality of primary subsets;
obtaining a second data set comprising a plurality of autonomous glucose measurements of the subject and, for each respective autonomous glucose measurement in the plurality of autonomous glucose measurements, a timestamp representing when the respective measurement was made;
obtaining a third data set from one or more insulin pens used by the subject to apply the insulin medicament dosage regimen, the third data set comprises a plurality of insulin medicament records, each insulin medicament record in the plurality of medicament records comprising:
(i) a respective insulin medicament injection event including an amount of insulin medicament injected into the subject using a respective insulin pen in the one or more insulin pens; and
(ii) a corresponding electronic timestamp that is automatically generated by the respective insulin pen upon occurrence of the respective insulin medicament injection event;
identifying the plurality of metabolic events using the plurality of autonomous glucose measurements of the subject and the respective timestamps in the second data set;
applying a first characterization to each respective metabolic event in the plurality of metabolic events, wherein the first characterization is one of insulin regimen adherent and insulin regimen nonadherent;
wherein:
(i) each metabolic event in the plurality of metabolic events is a fasting event and the prescribed insulin medicament dosage regimen is a basal insulin medicament dosage regimen, a respective metabolic event is deemed basal regimen adherent when the second data set includes one or more medicament records that establish, on a temporal and quantitative basis, adherence with the insulin medicament dosage regimen during the respective metabolic event, and a respective metabolic event is deemed insulin regimen nonadherent when the second data set fails to include one or more medicament records that establish, on a temporal and quantitative basis, adherence with the insulin medicament dosage regimen;
or wherein:
(ii) each metabolic event in the plurality of metabolic events is a meal event, and the prescribed insulin medicament dosage regimen is a bolus insulin medicament dosage regimen, a respective meal event is deemed insulin regimen adherent when one or more medicament records in the plurality of medicament records indicates in the third data set, on a temporal basis, a quantitative basis, adherence with the insulin medicament dosage regimen during the respective meal, and a respective meal is deemed insulin regimen nonadherent when the plurality of medicament records in the third data set fails to indicate adherence, on a temporal basis, and a quantitative basis with the insulin medicament dosage regimen during the respective meal;
combining the plurality of primary adherence values into a primary composite adherence value, wherein the combining downweights a first primary adherence value in the plurality of primary adherence values, representing a first primary time window in the plurality of nonoverlapping consecutive primary time windows, with respect to a second primary adherence value, representing a second primary time window in the plurality of nonoverlapping consecutive primary time windows, in calculating the primary composite adherence value, on the basis that the first primary time window occurs in time before the second primary time window;
generating and communicating the primary composite adherence value as a primary single representation to a display configured to display the primary composite adherence value along with a time period associated with the primary composite adherence value, thereby evaluating historical adherence to the standing insulin medicament dosage regimen for the subject; and
causing the display to provide a graphical user interface comprising a representation of the plurality of nonoverlapping consecutive primary time windows extending over at least the time period associated with the primary composite adherence value, each of said plurality of nonoverlapping consecutive primary time windows associated with a primary adherence value in the plurality of primary adherence values, and selectively providing, on the graphical user interface, the primary composite adherence value in an area separated from the representation of the plurality of nonoverlapping consecutive primary time windows.

14. The device of claim 1, wherein each autonomous glucose measurement is timestamped with a glucose measurement timestamp that represents when the measurement was made.

15. The device of claim 1, further comprising obtaining a plurality of insulin medicament administration records of the subject, each insulin medicament administration record in the plurality of insulin medicament administration records comprising an amount of insulin medicament administered to the subject and a corresponding timestamp that represents when the respective insulin medicament was administered, and
wherein classifying whether each respective metabolic event in the plurality of metabolic events is insulin regimen adherent or insulin regimen nonadherent is based on the insulin medicament administration records.

16. The device of claim 1, wherein the fasting event is identified in a respective time period by computing a moving period of variance $\sigma_k^2$ across the plurality of autonomous glucose measurements, where:

$$\sigma_k^2 = \left(\frac{1}{M} \sum_{i=k-M}^{k} (G_i - \overline{G})\right)^2$$

and where, Gi is the ith glucose measurement in the portion k of the plurality of glucose measurements, M is a number of glucose measurements in the plurality of glucose measurements and represents a contiguous predetermined time span, $\overline{G}$ is the mean of the M glucose measurements selected from the plurality of glucose measurements, and k is within the respective time period.

17. The method of claim 15, wherein the autonomous glucose measurements are obtained from one or more continuous glucose monitors, and the insulin medicament administration records are obtained from one or more insulin pens and/or pumps used by the subject to apply the insulin.

18. The device of claim 1, wherein identifying the plurality of metabolic events further comprises comparing the second data set to at least one other data set and removing data associated with at least one event that fails to temporally match between the second data set and the at least one other data set.

19. The method of claim 13, wherein identifying the plurality of metabolic events further comprises comparing the second data set to at least one other data set and removing data associated with at least one event that fails to temporally match between the second data set and the at least one other data set.

* * * * *